US006511814B1

(12) United States Patent
Carpenter

(10) Patent No.: US 6,511,814 B1
(45) Date of Patent: Jan. 28, 2003

(54) METHOD AND DEVICE FOR DETECTING ANALYTES IN FLUIDS

(75) Inventor: Charles R. Carpenter, Scarborough, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 0 days.

(21) Appl. No.: 09/439,024

(22) Filed: Nov. 12, 1999

Related U.S. Application Data

(63) Continuation-in-part of application No. 09/277,715, filed on Mar. 26, 1999.

(51) Int. Cl.[7] .................................................. G01N 33/567
(52) U.S. Cl. ............... 435/7.21; 435/287.1; 435/287.2; 435/286.5; 435/7.9; 435/7.1; 435/810; 435/970; 436/518; 436/528; 436/530; 436/541; 422/68.1; 422/70; 422/99
(58) Field of Search .................. 435/287.1, 287.2, 435/287.7, 286.5, 810, 970, 7.1, 7.9, 7.21; 436/518, 528, 530, 541; 422/68.1, 70, 99

(56) References Cited

U.S. PATENT DOCUMENTS

| | | | |
|---|---|---|---|
| 3,607,093 A | 9/1971 | Stone ........................... 23/253 |
| 3,615,222 A | * 10/1971 | Mead ........................... 23/230 |
| 3,791,933 A | 2/1974 | Moyer et al. ............... 195/127 |
| 3,801,466 A | 4/1974 | Denney ............... 195/103.5 R |
| 3,802,842 A | 4/1974 | Lange et al. ............. 23/253 TP |
| 3,811,840 A | 5/1974 | Bauer et al. ............. 23/253 TP |
| 3,819,488 A | 6/1974 | Rush et al. ........... 195/103.5 R |
| 3,902,052 A | 8/1975 | Amar et al. ........... 235/151.35 |
| 3,964,871 A | 6/1976 | Hochstrasser ........... 23/253 TP |
| 3,992,158 A | 11/1976 | Przybylowicz et al. . 23/253 TP |
| 4,042,335 A | 8/1977 | Clément ................. 23/253 TP |
| 4,059,405 A | 11/1977 | Sodickson et al. ........ 23/230 R |
| 4,061,468 A | 12/1977 | Lange et al. ............. 23/253 TP |
| 4,125,372 A | 11/1978 | Kawai et al. ............. 23/230 B |
| 4,160,008 A | 7/1979 | Fenocketti et al. ........... 422/56 |
| 4,233,029 A | * 11/1980 | Columbus .................... 23/230 |
| 4,277,561 A | 7/1981 | Monget et al. ............... 435/14 |
| 4,288,228 A | 9/1981 | Oberhardt ................. 23/230 R |
| 4,303,408 A | 12/1981 | Kim et al. ................. 23/230 B |
| 4,426,451 A | * 1/1984 | Columbus ................... 436/518 |
| 4,588,696 A | 5/1986 | Eskelson ..................... 436/130 |
| 4,594,327 A | 6/1986 | Zuk ............................ 436/514 |
| 4,627,918 A | 12/1986 | Saxena ....................... 210/656 |
| 4,637,978 A | 1/1987 | Dappen ........................ 435/11 |
| 4,654,127 A | 3/1987 | Baker et al. ................. 204/1 T |
| 4,717,656 A | * 1/1988 | Swanljung ..................... 435/7 |
| 4,734,360 A | * 3/1988 | Phillips ........................ 435/25 |
| 4,774,192 A | 9/1988 | Terminiello et al. ........ 436/530 |
| 4,790,979 A | 12/1988 | Terminiello et al. .......... 422/56 |
| 4,800,162 A | 1/1989 | Matson ....................... 435/280 |
| 4,812,400 A | 3/1989 | Steinman ..................... 435/21 |
| 4,839,297 A | 6/1989 | Freitag et al. ............... 436/170 |
| 4,857,453 A | * 8/1989 | Ullman et al. ................. 435/7 |
| 4,914,020 A | 4/1990 | Arai et al. ..................... 435/4 |
| 4,935,346 A | 6/1990 | Phillips et al. ................ 435/14 |
| 4,940,782 A | 7/1990 | Rup et al. .................... 530/387 |
| 4,943,522 A | 7/1990 | Eisinger et al. ................ 435/7 |
| 4,962,021 A | 10/1990 | Meserol et al. ................ 435/7 |
| 4,973,465 A | 11/1990 | Baurain et al. .............. 424/406 |
| 5,061,381 A | 10/1991 | Burd .......................... 210/789 |
| 5,082,626 A | 1/1992 | Grage et al. ................. 422/56 |
| 5,091,188 A | 2/1992 | Haynes ....................... 424/450 |
| 5,096,809 A | 3/1992 | Chen et al. .................. 435/7.9 |
| 5,104,793 A | * 4/1992 | Buck ......................... 435/7.92 |
| 5,104,812 A | * 4/1992 | Kurn et al. .................. 436/165 |
| 5,114,350 A | 5/1992 | Hewett ....................... 435/288 |
| 5,122,284 A | 6/1992 | Braynin et al. .............. 210/782 |
| 5,130,258 A | 7/1992 | Makino et al. .............. 436/169 |
| 5,141,850 A | * 8/1992 | Cole et al. ................... 436/525 |
| 5,147,606 A | 9/1992 | Charlton et al. .............. 422/56 |
| 5,186,844 A | 2/1993 | Burd et al. .................. 210/782 |
| 5,187,100 A | 2/1993 | Matzinger et al. ............ 436/16 |
| 5,212,060 A | 5/1993 | Maddox ...................... 435/7.1 |
| 5,242,606 A | 9/1993 | Braynin et al. .............. 210/787 |
| 5,252,293 A | 10/1993 | Drbal et al. ................. 422/101 |
| 5,304,348 A | 4/1994 | Burd et al. .................... 422/72 |
| 5,341,215 A | 8/1994 | Sehr .......................... 356/445 |
| 5,342,924 A | 8/1994 | Chang ........................ 530/387.9 |
| 5,389,524 A | 2/1995 | Larson et al. ................. 435/29 |
| 5,397,710 A | 3/1995 | Steinman ..................... 436/79 |
| 5,403,415 A | 4/1995 | Schembri ................... 156/73.1 |

(List continued on next page.)

FOREIGN PATENT DOCUMENTS

| | | |
|---|---|---|
| WO | WO 89/06138 | 7/1989 |
| WO | 91/18110 | 11/1991 |
| WO | WO 93/03176 | 2/1993 |
| WO | WO 94/20533 | 9/1994 |
| WO | WO 94/23300 | 10/1994 |

OTHER PUBLICATIONS

Patton, W.F.; *Biologist's Perspective on Analytical Imaging Systems as Applied to Protein Gel Electrophoresis*; Journal of Chromatography A, NL, Elsevier Science; vol. 698; No. 1; Apr. 28, 1995; pp. 55–87; XP004022952; ISSN: 0021–9673; abstract.

*Primary Examiner*—Christopher L. Chin
*Assistant Examiner*—Pensee T. Do
(74) *Attorney, Agent, or Firm*—Foley & Lardner

(57) ABSTRACT

A disposable, dry chemistry analytical system is disclosed which is broadly useful for the detection of a variety of analytes present in biological fluids such as whole blood, serum, plasma, urine and cerebral spinal fluid. The invention discloses the use of the reaction interface that forms between two liquids converging from opposite directions within a bibulous material. The discovery comprises a significant improvement over prior art disposable, analytical reagent systems in that the detectable reactant zone is visually distinct and separate from the unreacted reagents allowing for the use of reaction indicators exhibiting only minor changes as well as extremely high concentrations of reactants. In addition, staged, multiple reagents can be incorporated. Whole blood can be used as a sample without the need for separate cell separating materials. Finally, the invention is useful for the detection of analytes in a broad variety of materials such as milk, environmental samples, and other samples containing target analytes.

57 Claims, 35 Drawing Sheets

U.S. PATENT DOCUMENTS

| | | | |
|---|---|---|---|
| 5,408,535 A | 4/1995 | Howard, III et al. | 382/1 |
| 5,409,665 A | 4/1995 | Burd | 422/64 |
| 5,413,732 A | 5/1995 | Buhl et al. | 252/182.11 |
| 5,422,258 A | 6/1995 | Chang | 435/172.2 |
| 5,457,030 A | 10/1995 | Badal et al. | 435/34 |
| 5,472,603 A | 12/1995 | Schembri | 210/380.1 |
| 5,478,750 A | 12/1995 | Bernstein et al. | 436/164 |
| 5,518,930 A | 5/1996 | Burd | 436/45 |
| 5,543,144 A | 8/1996 | Chang | 424/133.1 |
| 5,563,042 A | 10/1996 | Phillips et al. | 435/14 |
| 5,591,643 A | 1/1997 | Schembri | 436/45 |
| 5,599,411 A | 2/1997 | Schembri | 156/73.1 |
| 5,601,991 A | 2/1997 | Oberhardt | 435/7.91 |
| 5,629,415 A | 5/1997 | Hollis | 536/23.53 |
| 5,653,980 A | 8/1997 | Hellman | 424/184.1 |
| 5,693,233 A | 12/1997 | Schembri | 210/787 |
| 5,716,852 A | 2/1998 | Yager et al. | 436/172 |
| 5,726,010 A * | 3/1998 | Clark | 435/5 |
| 5,726,013 A * | 3/1998 | Clark | 435/5 |
| 5,726,064 A * | 3/1998 | Robinson et al. | 436/514 |
| 5,750,333 A * | 5/1998 | Clark | 435/5 |
| 5,753,497 A * | 5/1998 | Bernstein et al. | 435/287.1 |
| 5,776,719 A | 7/1998 | Douglas et al. | 435/28 |
| 5,779,867 A | 7/1998 | Shieh | 204/403 |
| 5,802,842 A | 9/1998 | Hook et al. | 60/271 |
| 5,824,268 A | 10/1998 | Bernstein et al. | 422/56 |
| 5,856,203 A * | 1/1999 | Robinson et al. | 436/518 |
| 5,877,028 A * | 3/1999 | Chandler et al. | 436/514 |
| 5,948,684 A | 9/1999 | Weigl et al. | 436/52 |
| 5,962,336 A * | 10/1999 | Sun | 436/518 |
| 5,981,298 A * | 11/1999 | Chudzik et al. | 436/514 |
| 5,989,924 A * | 11/1999 | Root et al. | 436/518 |
| 5,998,221 A | 12/1999 | Malick et al. | 436/514 |
| 6,001,658 A * | 12/1999 | Frederickson | 436/514 |
| 6,007,999 A * | 12/1999 | Clark | 435/7.1 |
| 6,008,059 A * | 12/1999 | Schrier et al. | 436/518 |
| 6,027,944 A * | 2/2000 | Robinson et al. | 436/518 |
| 6,069,014 A * | 5/2000 | Schrier et al. | 436/518 |
| 6,136,610 A | 11/2000 | Polito | 436/514 |
| 6,222,619 B1 | 4/2001 | Herron et al. | 356/39 |
| 6,316,274 B1 | 11/2001 | Herron et al. | 436/518 |

* cited by examiner

Glucose Assay (Trinder Reagent Dried on Membrane)

Dried reagent streaking at reconstitution 246 mg/dL Glucose, T=0

T=5 Seconds

T=10 Seconds

Glucose Assay (Trinder Reagent Dried on Membrane)

T=20 Seconds

T=30 Seconds

T=2 Minutes

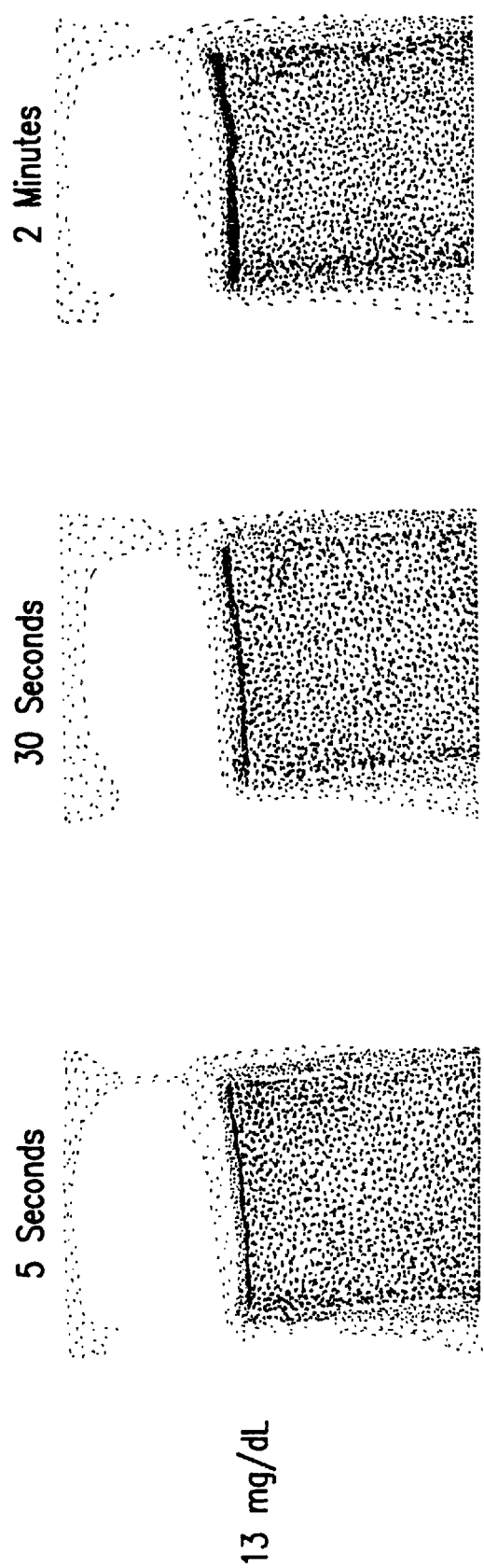

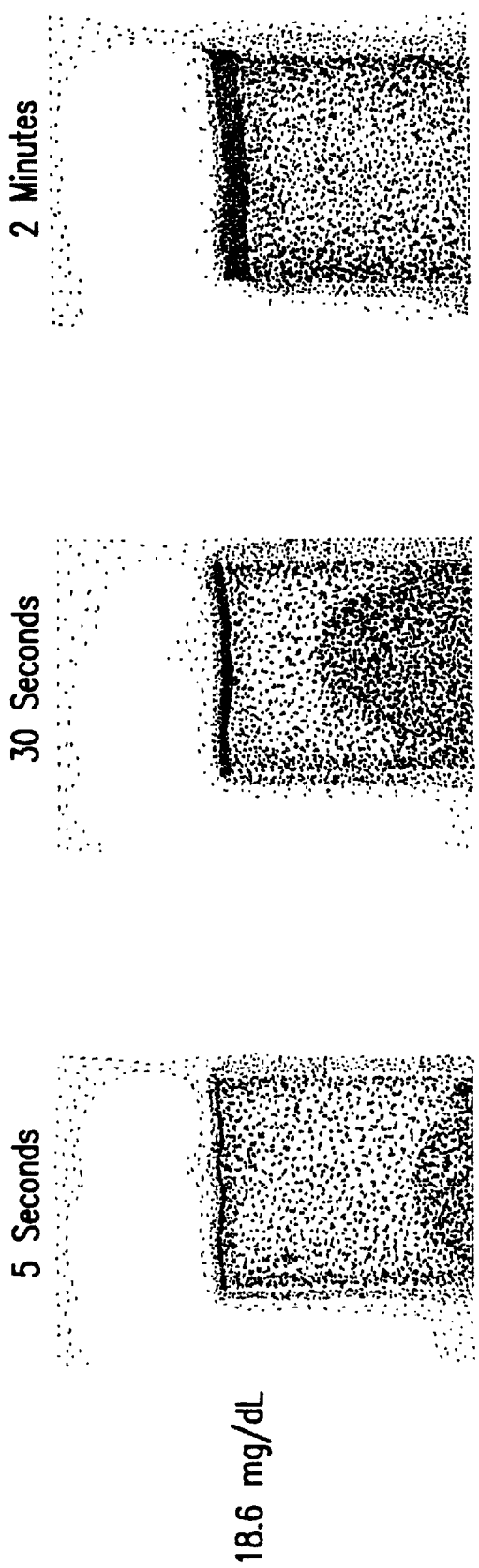

FIG. 21A

A. REACTION INTERFACE MAX DISTANCE TO SAMPLE EDGE AND $\Delta I/t$
B. REACTION INTERFACE MAX DISTANCE TO REAGENT EDGE AND $\Delta I/t$
C. LIQUID INTERFACE MAX DISTANCE TO SAMPLE EDGE AND $\Delta I/t$
D. LIQUID INTERFACE MAX DISTANCE TO REAGENT EDGE AND $\Delta I/t$
E. $\Delta$ LIQUID vs REACTION INTERFACE MAX AND $\Delta I/t$
F. REACTION INTERFACE MAX AT FIXED TIME POINTS
G. REACTION INTERFACE MAX $\Delta I/t$ (SLOPE)
H. REACTION INTERFACE AREA
I. LIQUID INTERFACE AREA
J. SAMPLE BACKGROUND
K. REAGENT BACKGROUND
L. LIQUID INTERFACE MAX $\Delta I/t$
M. REACTION INTERFACE, SHAPE OF CURVE A. REACTION INTERFACE MAX DISTANCE TO SAMPLE EDGE AND $\Delta/t$
B. REACTION INTERFACE MAX DISTANCE TO REAGENT EDGE AND $\Delta/t$
C. LIQUID INTERFACE MAX DISTANCE TO SAMPLE EDGE AND $\Delta/t$
D. LIQUID INTERFACE MAX DISTANCE TO REAGENT EDGE AND $\Delta/t$
E. $\Delta$ LIQUID vs REACTION INTERFACE MAX AND $\Delta/t$
F. REACTION INTERFACE MAX AT FIXED TIME POINTS
G. REACTION INTERFACE MAX $\Delta/t$ (SLOPE)
H. REACTION INTERFACE AREA
I. LIQUID INTERFACE AREA
J. SAMPLE BACKGROUND
K. REAGENT BACKGROUND
L. LIQUID INTERFACE MAX $\Delta/t$
M. REACTION INTERFACE, SHAPE OF CURVE

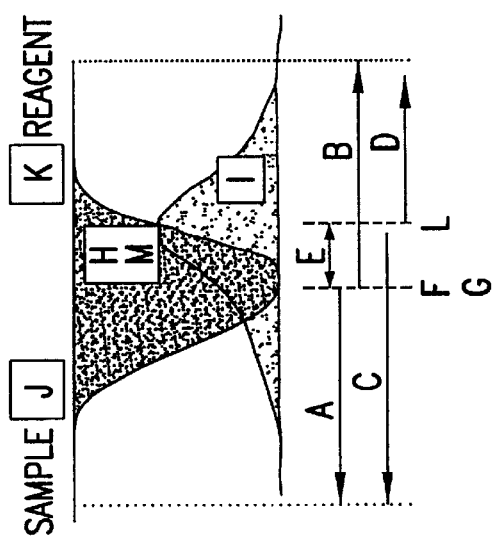

FIG. 21B

METHOD AND DEVICE FOR DETECTING ANALYTES IN FLUIDS

The present application is a continuation-in-part application of copending U.S. patent application Ser. No. 09/277, 715, which was filed on Mar. 26, 1999.

FIELD OF THE INVENTION

The present invention relates to test devices and methods for the determination of analytes which may be present in liquids.

BACKGROUND OF THE INVENTION

The quantification of chemical and biological components in aqueous sample solutions, such as whole blood, plasma, serum and urine, is important for the timely and correct diagnosis of various diseases, as well as for monitoring the progress of the medical treatment of diseases. In many cases the analytes being measured are present in only tiny amounts and are often mixed with much larger amounts of irrelevant or interfering components. Some components, such as red blood cells, prevent the analysis of the sample if they are present. Also problematic are the reagents and indicators used to detect and measure the analytes, which are often highly colored and closely resemble the reaction products in terms of their absorbance spectra. In addition, the measurement of analytes often requires multiple, incompatible reagents that must be stored separately and added sequentially. Any of these factors may complicate the detection and quantification of analytes in fluid samples.

These problems and issues have been addressed in a variety of ways. Analytical methods employed in clinical chemistry testing and other applications used can be divided into two broad categories of assay formats: liquid chemistry formats and dry chemistry formats. Liquid chemistry systems require that sample and liquid reagents be dispensed into reaction chambers in a timed, sequential order. Samples must often be diluted with special buffers to reduce or eliminate interfering compounds and are then added to reagents designed to react with specific analytes. In some cases, multiple reagents must be premixed immediately before use due to stability problems. In other cases additional reagents may be needed to provide color-producing, readable reactions. The results may be obtained by measuring the absorption of light by the fluid sample. Reactions involving decreases in reaction color or minor differences in color changes may further require separate tubes of reagents to standardize the results or serve as controls.

Dry chemistry systems utilize reagents dried onto absorbent surfaces. Most commercially available products have multiple layers of reactants sandwiched together. Some are arranged vertically and some combine vertical and horizontal arrangements. In all cases, dry chemistry systems using chromogenic reactions rely on measuring light reflected off of either the top or bottom surface of the final reagent pad. The assaying of whole blood presents additional problems since it requires a separate method for separating red blood cells from the sample such as centrifugation or the use of blood separating filter(s) which separate the plasma for analysis. The essence of dry chemistry analysis is to contain a liquid reaction so that colored reaction products can be visualized. This is done with gels and polymers, e.g., Vitros (Johnson & Johnson) or fibrous paper-like materials, e.g., Seralyzer (Bayer Diagnostics). In all cases the reaction must be observed among a mixture of sample, diluent, reactants and product which can result in difficulties distinguishing product from non-product. In addition, since all or part of the original reactant is consumed, it can be impossible to reference back to the starting material, such as to establish a reagent baseline. In contrast, the present invention retains all components for further evaluations.

In methods that require precise reaction timing, such as those requiring rapid reactions or measuring a rate of change, it is often difficult to determine the exact start time of the reactions. In most cases the performance of the assay, and therefore the reliability of the results, is dependent on the ability of the test system to evenly deliver a certain amount of liquid (usually blood plasma or serum) to a final reactant material. This material must absorb a known quantity of liquid with extreme accuracy and reproducibility in order for the results to be useful. The precise volume measurements required to obtain accurate results with these types of assays present particular challenges and make them difficult to work with.

Both liquid and dry chemistry systems are limited in the concentrations of reactants that can be used. These concentration limits are often due to the presence of highly colored reactants that absorb or reflect light at wavelengths that interfere with or obscure the detection of reaction product which may absorb or reflect light at similar wavelengths. Various methods have been employed in attempts to solve this problem. Hochstrasser, U.S. Pat. No. 3,964,871, describe a disposable indicator for measuring substances which registers the concentration of a substance in a given biological fluid with indicia which are directly readable in a convenient notation thereby reducing reliance on comparison with a color intensity scale. Kim et al., U.S. Pat. No. 4,303,408, describe elements with interferent-reducing zones which remove interferents prior to the reaction zone. Despite these attempts, only marginal improvements are possible due to the physical limitations which are inherent in the methods.

U.S. Pat. No. 5,716,852, issued to Yager et al., teaches a channel-cell system for detecting the presence and/or measuring the presence of analyte particles in a sample stream comprising a laminar flow channel, two inlets in fluid connection with the laminar flow channel for respectively conducting into the laminar flow channel an indicator stream which may comprise an indicator substance which indicates the presence of said analyte particles by a detectable change in property when contacted with said analyte particles, and the sample stream. The laminar flow channel has a depth sufficiently small to allow laminar flow of streams and a length sufficient to allow particles of the analyte to diffuse into the indicator stream to the substantial exclusion of the larger particles in the sample stream to form a detection area. An outlet conducts the streams out of the laminar flow channel to form a single mixed stream. Yager discloses the formation of a reaction interface that forms between two fluids moving through a capillary tube in the same direction. We disclose the invention of a stable interface that forms when two liquids meet and stop in a flow matrix after conveying from opposite directions. The Yager patent is predicated on the principle of liquid laminar flow, which was known in the art. In contrast, the present invention employs bibulous material to physically contain the liquid interface.

U.S. Pat. No. 5,187,100, issued to Matzinger et al., discusses a control solution for use with a porous reagent strip, and comprises a flexible semisolid polymer dispersed in water, such as polyvinyl acetate in distilled water, with appropriate control glucose concentration levels. This solution is useful in mimicking whole blood in conjunction with porous reagent strips to determine compliance of the strips and meters to established measurement and performance criteria.

U.S. Pat. No. 5,147,606, issued to Charlton et al., teaches a diagnostic device that detects blood analytes with a sample volume as low as 2 microliters in the hematocrit range of 0% to 60%, or higher. This is accomplished by employing a housing with various chambers and compartments for processing the blood. A sample application port in the housing is used to introduce blood into a metering chamber. From the metering chamber, the blood flows to a reaction chamber for analyzing blood analytes. Blood entering the metering chamber flows into a fluid capillary which indicates that an adequate amount of blood has been received in the metering chamber. The reaction compartment includes a reagent and a filter, the latter of which is disposed between the metering chamber and the reagent so that the reagent reacts with the filtered blood.

U.S. Pat. No. 4,839,297, issued to Freitag et al., teaches a test apparatus for the analytical determination of a component of a body fluid with a base layer and at least two planar test layers which, in the initial state of the test carrier, before carrying out the determination, are separate from one another but can be brought into contact with one another by external manipulation. A first test layer and a second test layer are arranged on the base layer essentially next to one another but separated in the initial state by a gap, a contact element being provided which consists of a capillary-active material which is so dimensioned that it can bridge the gap and which is so mounted and arranged that, in a first position, it cannot contact at least one of the test layers but, by external pressure, it can be brought into a second position in which it contacts both test layers in such a manner that a liquid exchange between the test layers is possible.

U.S. Pat. No. 4,637,978, issued to Dappen, discloses an assay useful for the determination of an analyte in whole blood. In particular, this assay is useful for the quantitative determination of peroxide-generating analytes, such as glucose or cholesterol, in whole blood. This assay utilizes a multizone element consisting essentially of a support having thereon, in order and in fluid contact, a registration zone and a reagent/spreading zone. The reagent/spreading zone has a void volume and average pore size effective to accommodate whole blood, and contains an interactive composition necessary for the analysis. Such composition is capable of providing, upon interaction with the analyte, a dye which can be spectrophotometrically detected at a wavelength greater than about 600 mm.

U.S. Pat. No. 5,408,535, issued to Howard, III et al., discloses a video test strip reader which can simultaneously locate, color analyze and time-track multiple reagent test strips, such as those used in solid-based clinical assays. The reader includes a video imager that produces an analog signal which is converted into a digital signal representing the image. The digital signal is stored in the form of arrays of pixels containing color information. The digital signal is then processed to calculate the desired test results, such as the concentration of a constituent or other measurable properties.

U.S. Pat. No. 4,160,008, issued to Fenocketti et al., teaches a test device for determining the presence of a liquid sample constituent. The device comprises a base support member having attached to it an indicator member which produces a detectable response, such as a color change, in the presence of the sample constituent. The indicator member comprises an upper reagent layer, a lower absorbent layer and a substantially sample-impervious barrier layer between the upper and lower layers. The indicator member is attached to the base member along the lower side of the absorbent layer.

U.S. Pat. No. 4,042,335, issued to Clement, discloses a multilayer element for the analysis of liquids such as biochemical and biological liquids. The invention includes a reagent layer including a composition that is interactive in the presence of a predetermined substance to be analyzed (analyte) to provide a diffusible, detectable species, e.g., a dye, can be detected. Preferably between the reagent layer and the registration layer, there can be a radiation-blocking layer, such as an opaque reflecting layer, to enhance detection of the diffusible species within the registration layer. A spreading layer is separated from the registration layer by a reagent layer. In operation, a sample of liquid under analysis is applied to the reagent layer or, if present, to a spreading layer. If the sample contains analyte, a chemical reaction or other interaction within the reagent layer provides a detectable species that diffuses, via any intervening layers such as a radiation-blocking layer, into the registration layer for detection there, such as by radiometric techniques like reflection spectrophotometry.

U.S. Pat. No. 3,992,158, issued to Przybylowicz et al., discloses an integral analytical element capable of use in the analysis of liquids, the element having at least two superposed layers including a spreading layer and a reagent layer, in fluid contact. The spreading layer, which can be an isotropically porous layer, spreads within itself at least a component of a liquid sample applied to the element, or a reaction product of such component, to obtain a uniform concentration of at least one such spread substance at the surface of the spreading layer which faces the reagent layer. The reagent layer, which preferably is uniformly permeable to at least one dissolved or dispersed component of the liquid sample or a reaction product of such a component, can include a matrix in which is distributed a material that can interact with, for example, an analyte or analyte reaction product to produce a detectable change in the element, such as one detectable by measurement of electromagnetic radiation. In a preferred embodiment, the interactive material can chemically react with an analyte or analyte reaction product to produce a color change in the element. In another preferred embodiment, the sample spreading layer can filter out chemically interfering or other undesirable materials and obtain selective spreading of sample components and/or it can provide a reflective background, often useful in obtaining analytical results.

U.S. Pat. No. 3,811,840, issued to Bauer et al., teaches a test device for detecting low concentrations of substances in test fluids which includes an absorbent wick having a substantially flat surface portion enclosed in a fluid impervious sheath having an aperture of predetermined limited area formed therein. The aperture is contiguous to and exposes a predetermined limited area of the flat surface portion of the wick, which is incorporated with a reagent specifically reactable with the substance being detected. In use the device is immersed into the test fluid so that the aperture is submerged and the device is allowed to remain therein while the test fluid contacts the reagent area adjacent to the aperture and migrates into the remainder of the wick. The reagent is immobilized with respect to the liquid.

U.S. Pat. No. 4,061,468, issued to Lange et al., discloses a test strip for the detecting of components in liquids, especially in body fluids. The test strip includes a holder and at least one indicator layer containing detection reagents. One surface of the indicator layer is attached to the holder and the other surface is covered with a fine meshwork.

Note, however, that the analytical devices of the above prior art employ fluid movement in only a single direction. Because no reaction interface is created by a movement of two fluids in opposite directions, the above prior art references cannot be employed to measure the reaction intensity or reaction rate at a reaction interface, as disclosed by the present invention.

The present invention provides a solution to the problems and deficiencies of current systems discussed above. Specifically, the present invention provides devices which contain all reactants necessary for sample preparation and analyte detection and methods for their use. The present invention provides devices and methods which eliminate the extreme precision in volume measurement which is required by some methods. The results of assays conducted with the present invention are read in a generic reading area of the device, and a wide variety and versatility in reagent chemistry and concentrations is offered.

SUMMARY OF THE INVENTION

The present invention provides a device for detecting and quantifying at least one analyte in a fluid sample suspected of containing the analyte by employing a liquid reactant capable of reacting with the analyte to form a detectable soluble reaction product. The device comprises a fluid transport material having a first zone ("fluid sample zone") for the application of the fluid sample at a fluid sample application site and a second zone ("liquid reactant zone") for the application of a liquid reactant at a liquid reactant application site, wherein when the fluid sample is added to the first zone, and the liquid reactant is added to the second zone, the fluid sample flows in a first direction from a fluid sample edge toward the second zone, and the liquid reactant flows in a second direction opposite to that of the first direction and toward the first zone from a liquid reactant edge. When the flowing fluid sample and the flowing liquid reactant meet, flow stops, the reactants diffuse toward one another, and the detectable reaction product is formed by a reaction between the liquid reactant and the analyte at a stable reaction interface formed at a juncture between and visually distinct from the fluid sample and the liquid reactant.

In another embodiment, the present invention also provides a device for detecting and quantifying at least one analyte in a fluid sample suspected of containing the analyte, comprising a fluid transport material having a first zone ("fluid sample zone") for the application of the fluid sample at a fluid sample application site and a second zone ("liquid reactant zone") for the application of a liquid reactant at a liquid reactant application site, wherein the reagent and the liquid form a liquid reagent containing a reactant reagent capable of reacting with the analyte present in the fluid sample to form a detectable reaction product, wherein when the fluid sample is added to the first zone, and the liquid reactant is added to the second zone, the fluid sample flows in a first direction from a fluid sample edge toward the second zone, the reagent is reconstituted and the reagent and the liquid form a liquid reagent containing a liquid reactant capable of reacting with the analyte to form a detectable reaction product, and the liquid reactant flows in a second direction opposite to that of said first direction and toward said first zone from a liquid reactant edge. When the flowing fluid sample and the flowing liquid reactant meet, flow stops, the reactants diffuse toward one another, and the detectable reaction product is formed by a reaction between the liquid reactant and the analyte at a stable reaction interface formed at a juncture between and visually distinct from the fluid sample and the liquid reactant.

The fluid transport material used in the present invention is preferably capable of transporting the fluid sample and the liquid reagent by supporting capillary action and thereby facilitating the movement of fluid sample through the material. Further, the fluid transport material is preferably capable of maintaining a defined interface with little mixing of the opposing liquids while allowing diffusion to occur. In a particularly preferred embodiment, the fluid transport material comprises a nitrocellulose material cast onto a polyvinylchloride or polyester (i.e., Mylar™) backing material.

One or more reconstitutable reagents may be contained on the bibulous material in one or more reagent zones. Reagents to be reconstituted by the fluid sample may be located on the fluid transport material at a site which is closer to the application site for the fluid sample than to the application site for the diluent solution. Conversely, reagents which are to be reconstituted by the diluent solution may be located on the fluid transport material at a site which is closer to the application site for the diluent solution than to the application site for the fluid sample. Fluid flow through these reagent zones reconstitutes the reagents, effectively pretreating the sample or mixing and/or reacting one reagent with another. In other embodiments, the reagent or reagents may be contained in an absorbent pad placed in contact with the fluid transport material at the liquid reagent zone. The absorbent pad may be selected from the group consisting of cellulose, glass fiber, polyester, or any absorbent polymer. An absorbent pad may be placed onto the fluid sample application site to pretreat the fluid sample before it enters the absorbent material, e.g., to remove red blood cells from a red blood cell-containing sample. The reagent or reagents may be present in a plurality of locations on the fluid transport material.

In another embodiment, the fluid transport material may be capable of separating red blood cells from whole blood as the fluid sample travels through the bibulous material. In various embodiments the fluid transport material may be a HEMASEP L® membrane, a HEMASEP V® membrane, or a SUPOR® membrane (each available from Pall-Gelman, Port Washington, N.Y.), a CYTOSEP® membrane (Allstrom Filtration, Mount Holly Springs, Pa.), or a nitrocellulose membrane.

The amount of analyte present in the sample is determined by measuring the amount of detectable reaction product, and determining from the measured amount of reaction product the amount of analyte. The detectable reaction product may be measured by any appropriate means known to those in the art. For example, if the reaction product absorbs light at a particular wavelength, the absorbance at that wavelength may be measured and related to the amount of analyte. The reaction product may alternatively, as appropriate, be measured by transmission, reflectance, fluorescence, luminescence, or by electrochemical methods, e.g., electrical conductance.

The concentration of unreacted reagents on the fluid transport material may provide a reference value, control, or blank for the assay. The concentration of unreacted sample on the bibulous material may also provide a reference value, control, or blank for the sample, e.g., a red blood cell-containing sample can be checked for hemolysis. The device of the present invention may further contain a means for calibrating a concentration of the liquid reagent, by adding an amount of analyte at a point adjacent to but distinct from the point in the first zone at which the fluid sample is added, such that the analyte and the liquid reactant meet and produce a detectable calibration product. The device of the present invention may further comprises a means for simultaneously applying the fluid sample to the first zone and the liquid reactant to the second zone and a sensor effective to detect the detectable reaction product. The sensor may be, for example, a CCD imaging camera or a optical imaging device.

The present invention also provides a method for detecting and quantifying at least one analyte in a fluid sample suspected of containing the analyte by employing a liquid reactant capable of reacting with the analyte to form a detectable soluble reaction product. The method includes the steps of providing a fluid transport material having a first zone ("fluid sample zone") for the application of the fluid sample at a fluid sample application site, and a second zone ("liquid reactant site") for the application of the liquid reactant at a liquid reactant application site, adding the fluid sample to the first zone and the liquid reactant to the second zone, whereupon the fluid sample flows in a first direction from. a fluid sample edge toward the second zone, and the liquid reactant flows in a second direction opposite to that of the first direction and toward the first zone from a liquid reactant edge. When the flowing fluid sample and the flowing liquid reactant meet, flow stops, the reactants diffuse toward one another, and the detectable reaction product is formed by a reaction between the liquid reactant and the analyte at a stable reaction interface formed at a juncture between and distinct from the fluid sample and the liquid reactant. The detectable reaction product is then detected and optionally measured. The detectable reaction product may be detected and optionally measured by any appropriate method, such as, for example, absorbance, fluorescence, luminescence, transmission, or electrochemical parameters, such as changes in conductance.

The reagent may be a plurality of reagents in a plurality of locations on the fluid transport material. The fluid sample may be whole blood, blood plasma, blood serum, urine, or any body fluid. In addition, the invention is useful for the detection of analytes in a broad variety of materials such as milk, environmental samples, and other samples containing target analytes. The reagents may further be added to either or both of the fluid sample and diluent solution prior to contact with the fluid transport material. In this aspect, the methods include providing a fluid transport material as described above, and the bibulous material may contain no reagents or may contain additional reagents, either dried into the fluid transport material or into a pad contacting the fluid transport material.

The above and other objects, features and advantages of the present invention will become apparent from the following description read in conjunction with the accompanying drawings.

BRIEF DESCRIPTION OF THE DRAWINGS

FIGS. 5A–5I are photographs showing results over time of three concentrations of calcium assays performed with the present invention.

FIG. 21 is a schematic representation of the various parameters that can be measured in the methods and devices of the present invention.

DETAILED DESCRIPTIONS OF THE INVENTION

Figure 1:
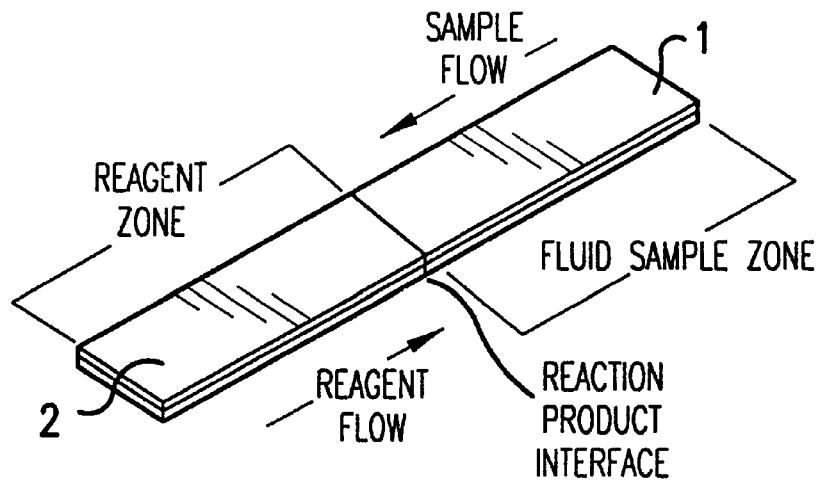
FIG. 1 is an isometric view of the test strip of the present invention showing locations of application sites for fluid sample and diluent solution, direction of diluent solution and fluid sample flow, and reaction product location after completion of the test.

The present invention provides devices for detecting analytes which may be present in a fluid sample, by reacting a liquid reactant with the fluid sample and forming a detectable reaction product. The device of the present invention comprises an absorbent strip made of a fluid transport material ("bibulous material") which is capable of absorbing and transporting fluid sample, reagents, and diluent liquids via capillary action. Analytical reagents capable of being dissolved and distributed within the absorbent strip may,be dried into the absorbent strip or into reagent pads in contact with the absorbent strip. The device of the present invention is particularly useful for clinical chemistry applications.

We have observed the unexpected result that two liquids converging from opposite ends of a bibulous material meet at a very sharply defined interface, with little mixing of the two opposing solutions over periods of time amounting to several minutes. This allows the creation of a stable reaction interface where the two opposing liquids containing reagents or analytes capable of reacting with each other meet, diffuse, and form a detectable product. The resulting product is localized at the interface for a significant period of time, allowing analysis of the reaction rate and the reaction product band intensity without the need to measure starting reagent volumes. Since the reaction product is visually distinct from the reactants, high concentrations of reactants may be used. This allows for the use of large amounts of certain reagents which can counteract endogenous interfering compounds without obscuring results due to closely related absorbency spectra or density of unreacted reagents. The present invention comprises a significant improvement over prior art disposable, analytical reagent systems in that the detectable reactant zone is distinct and separate from the unreacted reagents, allowing for the use of reaction indicators exhibiting only minor changes as well as extremely high concentrations of reactants.

Because the reactants, i.e., the fluid sample and the liquid reactants, are visually distinct from the reaction product, the system contains a built-in sample of both the unreacted fluid sample and the unreacted liquid reactant solution. These may be used as references for certain types of analytical reactions, such as those involving density changes and not spectral changes, or those requiring a starting reagent or reference value.

The devices of the present invention may be made of any material which is capable of absorbing liquids and causing capillary flow from areas of high concentration to areas of low concentration on the device, while maintaining a defined reaction product interface with little mixing of the opposing liquids. The materials of the device may be made of nitrocellulose membranes, cellulose sheets, porous polyethylene, polyethersulfone, or membranes of a variety of other materials. Porous plastics made from a variety of polymers may also be used, such as polyethylene, polystyrene, or polypropylene. Most preferable are bibulous materials made from nitrocellulose cast onto a backing material, such as PVC or Mylar™ (or another polyester film). An example of this type of bibulous material is that available from Schleicher and Schuell, catalog no. FF-170. When using nitrocellulose, the nitrocellulose materials should be first pretreated to render the membranes hydrophilic. The fluid transport material may be adhered to a solid backing, such as PVC or polystyrene, in order to provide durability in handling. These materials are provided by way of example, and are not intended to be limiting. The person of ordinary skill will realize that a variety of materials may be successfully utilized in the present invention, so long as the material has the properties of being able to absorb the sample, support capillary action and thereby facilitate the movement of fluid sample through the material, and maintain a defined interface with little mixing of the opposing liquids.

Regarding hydrophilic absorbent materials, two factors affect usefulness in the present invention. First, the pore size affects the integrity of the reaction interface. As pore size increases, the reaction interface spreads and becomes more diffuse. Second, as the percent solids (v/v) in the membrane increases, the signal intensity of the reaction interface decreases, presumably due to the lower volume of the reaction liquid at the interface. Preferably, the pore size is on the order of 5 $\mu$m, based on currently available materials. It is conceivable that a material of small pore size and low solid may be an excellent material.

In preferred embodiments for assaying samples containing whole blood or blood products containing unwanted red blood cells, the fluid transport material may be a material which separates plasma or the blood product from red blood cells. In these embodiments, the fluid transport material may be a HEMOSEP V® or HEMOSEP L® membrane (available from Pall-Gelman Inc., Port Washington, N.Y.) or a CYTOSEP® membrane (available from Allstrom Filtration, Mount Holly Springs, Pa.).

The methods and devices of the present invention provide for sample preparation and analysis to be performed in one step on the same device. The device may be a strip in the form of a generally rectangular shape. Alternatively, the bibulous material may also be a circular or linear array or star-shaped configuration which has the additional advantage of allowing multiple analytes to be analyzed in a single assay. Of course, the person of ordinary skill will realize that the bibulous material may be of any shape advantageous under the particular circumstances.

Figure 2:
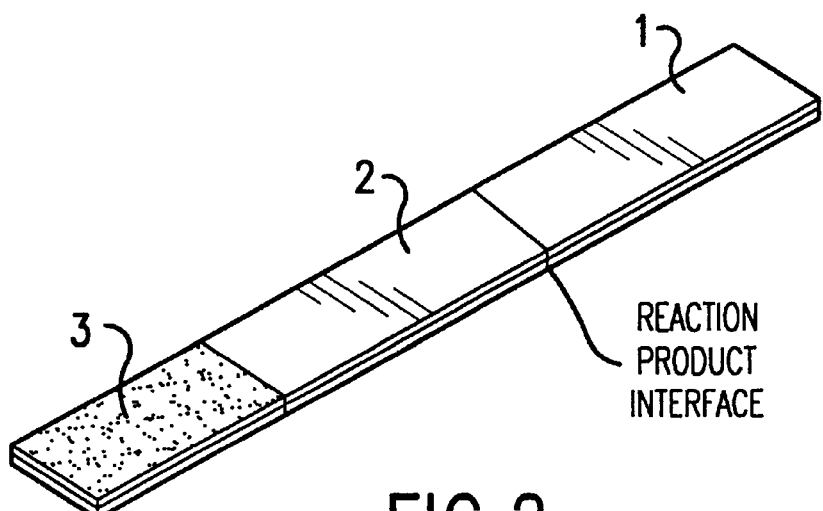
FIG. 2 is an isometric view of another embodiment of the present invention, in which a dried reagent pad containing one or more reagents is attached to one end of the test strip, and the diluent solution application site is located on a portion of the dried reagent pad.

The present invention can employ reagent systems capable of performing chemical evaluation of analytes which are commonly present in biological fluids. Such reagent systems are widely known in the art. Of particular interest are those reagent systems utilizing a single component, i.e., where the reaction occurs in a single solution, rather than those requiring more than one timed incubation step. The present invention provides single-component reagent systems composed of several different chemical reagents where the reagents are dried in spatially separated zones on the strips. As shown in FIGS. 1 and 2, dried reagent strips of the present invention may be used by applying a diluent solution ("diluent solution" is defined as any liquid capable of dissolving a reagent. Any reagents which are added to the diluent solution or reconstituted by the diluent solution, are meant to be included in the definition as part of the diluent solution) to one end of the strip and a fluid sample ("fluid sample" is defined as any fluid containing an analyte to be assayed for. Any reagents which are added to the fluid sample, or reconstituted by the fluid sample, are meant to be included in the definition as part of the fluid sample) to be assayed to the other end. Referring to FIG. 1, the fluid sample may be applied to the fluid sample application site 1 in the fluid sample zone ("fluid sample zone" is defined as any area on the bibulous material which is closer to the fluid sample application site than to the liquid reactant application site) and the liquid reactant may be applied to the liquid reactant application site 2 in the liquid reactant zone ("liquid reactant zone" is defined as any area on the bibulous material which is closer to the liquid reactant application site than to the fluid sample application site). As the two liquids move toward each other through the strips the sample may separate into components. For example, when cell separating strips are used, the fluid sample may separate into plasma and red blood cells. The fluid sample may also reconstitute one or more reagents as it moves through the fluid transport material, thereby pre-treating the sample before the final reactions occur. The liquid reactant simultaneously travels from the opposite end of the strip, and may optionally dissolve in sequence one or more dried reagents which may be present in the liquid reactant zone of the strip. When the fluid sample and the liquid reactant meet, a reaction interface forms between the conveying liquids. The reaction products occupy a very narrow band at the interface and are measured for rate and intensity of formation. Usually, the increase in the amount of product formed (or of decrease in the amount of reagent and/or analyte supplied) will be measured as a function of time. Alternatively, the amount of the product, reagent and/or analyte may be measured at one or more fixed time points. The change in the amount of product formed is typically measured by measuring the increase or decrease in absorbance over time at a wavelength at which the maximal absorbance is detected. In a preferred embodiment, the reaction products will be measured using reflection. However, the person of ordinary skill will realize that other means of measuring the reaction products may also be utilized, such as through the use of electrochemical methods (e.g., measuring changes in conductance), fluorescence, luminescence, transmission or other methods known in the art which provide a detectable signal related to the presence and/or the amount of a reaction product. The resulting reactant band is stable over several minutes, with little product diffusion into the surrounding area, which allows adequate time for the determination of rate and intensity of color development.

FIG. 2 illustrates another embodiment of the invention where one or more reagents which may be present on the bibulous material may be present in the form of a dried reagent pad 3. In this embodiment, dried reagent pad 3 is located on a portion of the diluent solution application site 2.

The fluid sample application site may further contain one or more pads for processing the fluid sample prior to its exposure to the reagent. As an example, the fluid sample application site may contain a blood sample-processing pad for pretreatment of whole blood samples or whole blood-containing samples. Examples of such pads include Hemasep-L or, more preferably, Hemasep-V (Pall Corporation) or glass fiber. In addition, the reagent application site furthermore may incorporate a pad containing a dried reagent capable of being reconstituted by addition of a diluent. This replaces the requirement for application of a liquid reagent with the far simpler reconstitution of a dried reagent using a diluent.

In some cases, it may be preferable to measure the disappearance of a reagent or analyte, rather than the appearance of a product. For example, reduced nicotinamide adenine dinucleotide (NADH), a cofactor for many enzymes, absorbs light much more strongly at 340 nm than when in its oxidized form, NAD. Accordingly, when measuring the activity of an enzyme that uses NADH as a cofactor, it may be advantageous to measure the reduction in absorbance at 340 nm. Alternatively, the formation of NADH may be measured as an increase in absorbance at 340 nm.

Figure 3:
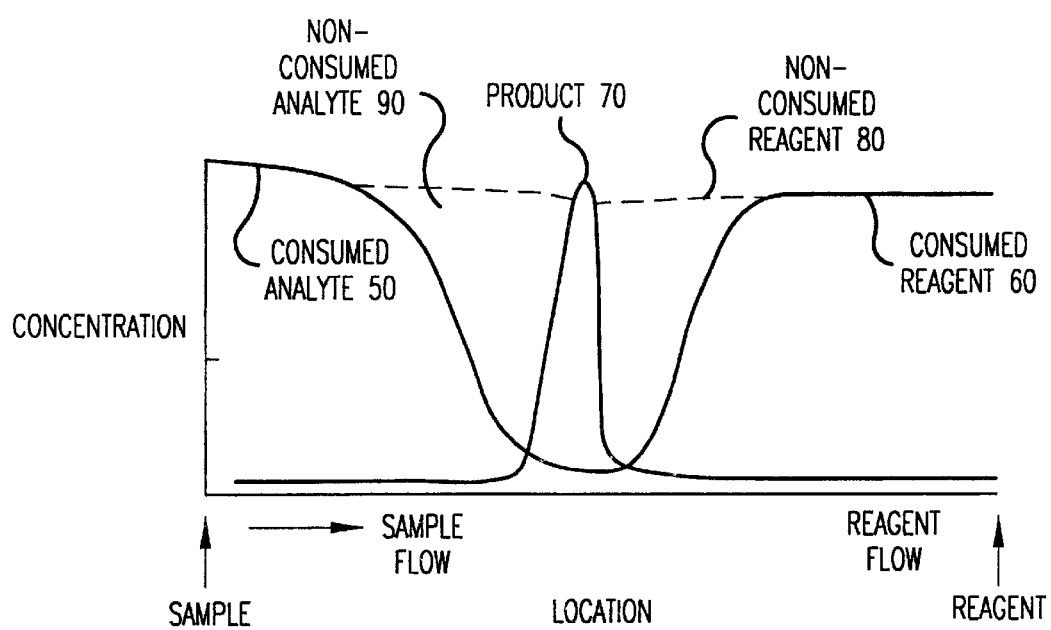
FIG. 3 is a schematic representation of the concentrations of analyte, reagent, and reaction product at locations along the bibulous material and illustrates that at the interface, the concentration of unreacted analyte and reagents falls sharply as they react and form reaction product, and that the concentration of reaction product correspondingly rises sharply at the interface.
Figure 4A:
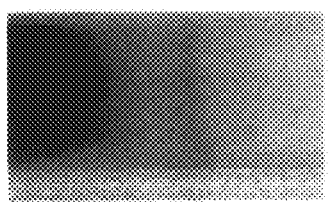
FIGS. 4A–4F are photographs showing results over time of a glucose assay performed with the present invention.
Figure 4B:
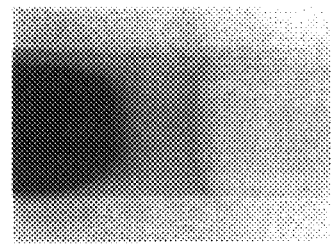
Figure 4C:
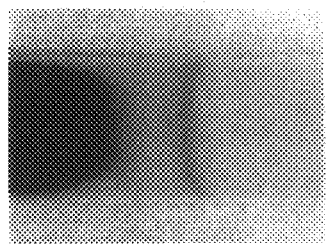
Figure 4D:
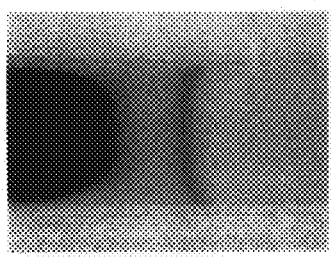
Figure 4E:
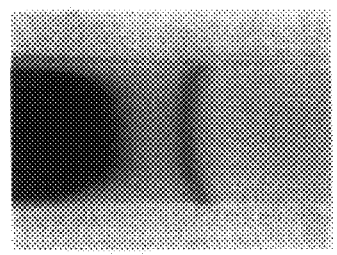
Figure 4F:
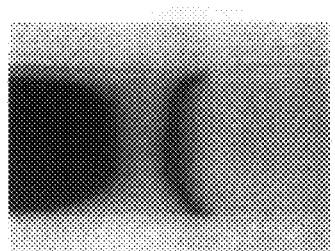
Figures 5A, 5B, 5C:
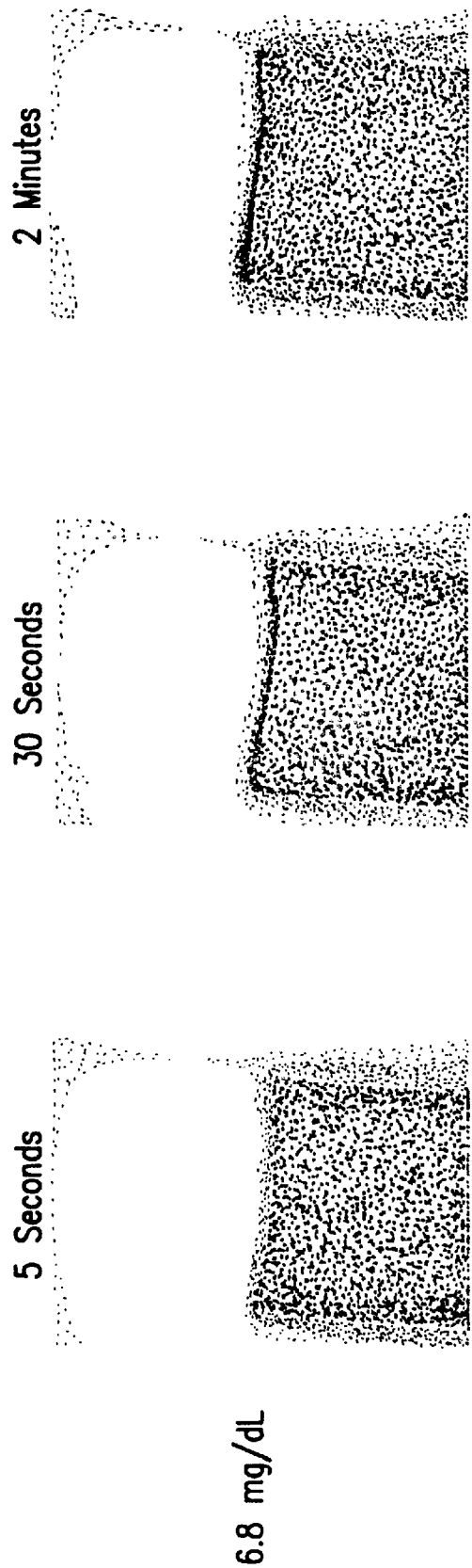
Figure 6:
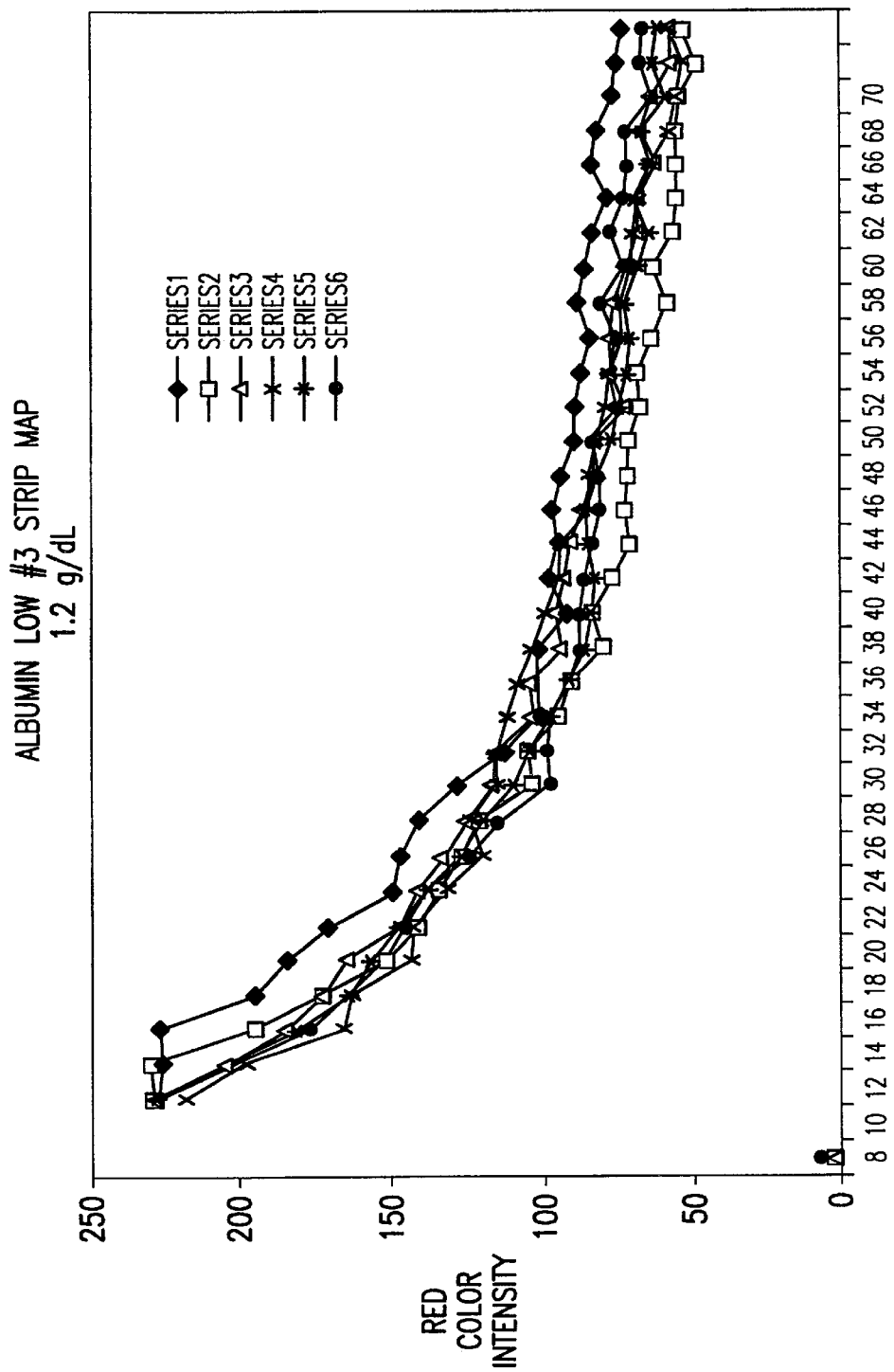
FIG. 6 is a graph of color intensity versus time for six independently read reflective values of a reaction interface from a sample having an albumin concentration of 1.2 g/dl based on an assay run with the present invention.

FIG. 3 is a graphical illustration showing hypothetical relative concentrations of analyte to be assayed, reaction product, and reactant at locations along the bibulous material. The relative concentrations illustrated may be typical of those found on the bibulous material during an assay. FIG. 3 is illustrative of four types of assays which may occur on the bibulous material. Line 70 represents product formed. Lines 50 and 60 signify "consumed analyte" and "consumed reagent", respectively, and may illustrate a reaction where the reagent or the analyte is consumed, such as a dye-binding assay where dye is bound to an analyte and both dye and analyte are "consumed" in the complex when the reaction occurs. At the reaction interface, concentrations of unconsumed analyte and unconsumed reagent fall sharply as the concentration of reaction product rises sharply. In other types of reactions, reagent is not consumed in the reaction. For example, in enzymatic assays the enzyme is not consumed but simply converts an analyte (or substrate) to a detectable product. In this case the non-consumed reagent is represented by line 80 and the consumed analyte by line 50. In another type of assay, reagent may be consumed and analyte not consumed such as for a serum enzyme (represented by line 90). There are thus four types of assays which may occur and which are illustrated by FIG. 3: those where analyte is consumed and reagent not consumed, those where analyte is not consumed and reagent is consumed, and those where analyte and reagent are both consumed or not consumed.

Because the reaction interface remains visually distinct from the fluid sample and reagent solution on the bibulous material, the device incorporates a built-in methodology for determining both reagent and fluid sample concentrations and dilutions. Where dried reagents are reconstituted, the device also provides for the internal calculation of reference values which take into account the extent of dilution of reagents in the diluent solution and in the fluid sample (i.e., reflecting the extent to which the dried reagents which may be present have dissolved in the diluent solution or the fluid sample), and for the measurement of background signal, all of which may be useful in certain types of analytical chemistry formats. For example, certain fluid samples may contain material that reflects light at a wavelength at or close to that of the reaction product and this signal must therefore be subtracted from the final reaction product color intensity. In other formats, e.g., where results are directly related to reagent concentration, for example in rate reactions where the analytes are in excess, a simultaneous measurement of both starting reagent concentration and product concentration by reflected light intensity at different wavelengths allows adjustment of the resulting analyte concentration values based on variability in the extent of reagent dissolution. A person of ordinary skill in the art would recognize that the method of the present invention permits the measurement of numerous other parameters that may be useful in measurements of operational stability, as well as calibration or calculation of background or reference values. Example of such parameters include, without limitation:

1. the distance between a sample application site edge and the reaction interface, and the change of the distance over time (A in FIG. 21);
2. the distance between a reagent application site edge and the reaction interface, and the change of the distance over time (B in FIG. 21);
3. the distance between a sample application site edge and the liquid interface, and the change of the distance over time (C in FIG. 21);
4. the distance between a reagent application site edge and the liquid interface, and the change of the distance over time (D in FIG. 21);
5. the distance between the reaction interface and the liquid interface, and the rate of change in the distance over time (E in FIG. 21);
6. the area of the liquid interface (I in FIG. 21);
7. the absorbance or reflectance of the sample background (J in FIG. 21);
8. the absorbance or reflectance of the reagent background (K in FIG. 21); and
9. the absorbance or reflectance of the liquid interface, and the rate of change in the same parameter over time (L in FIG. 21).

Figure 22:
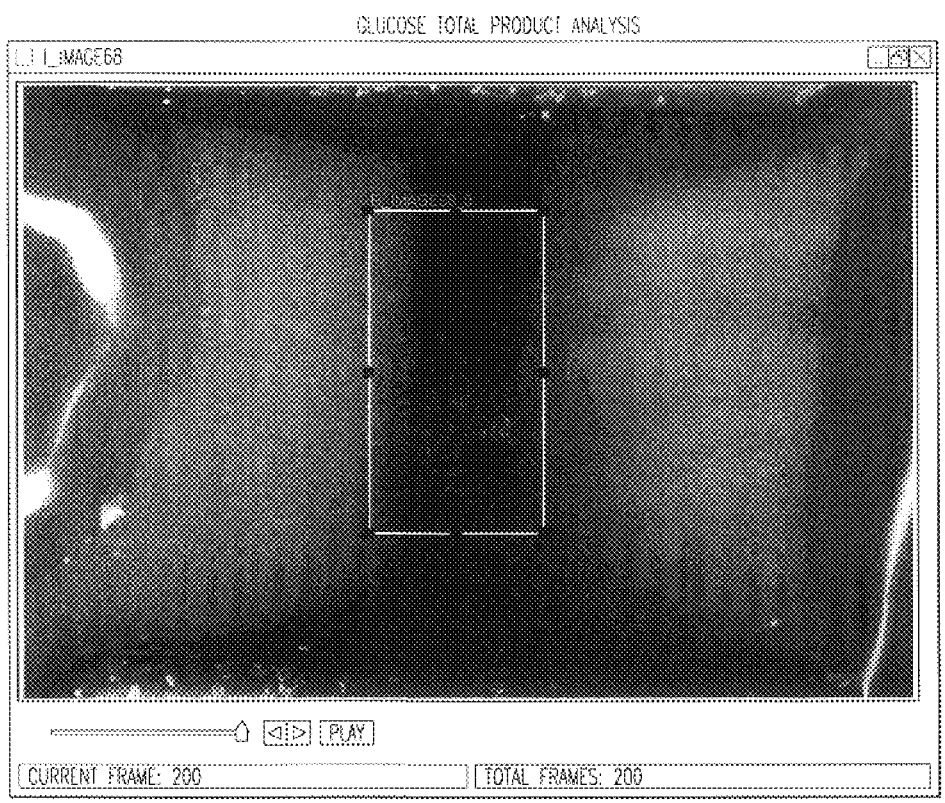
FIG. 22 is a schematic representation of the measurement of a portion of the area of the product interface region as a measurement of bioactivity in an assay of glucose concentration.

Clinical chemistry assays, whether they are liquid- or solid-based, can be read by kinetic analysis (rate of product formation; G in FIG. 21) or end-point analysis (amount of production at one or more given time points, F in FIG. 21). Preferably, the detectable reaction product is measured by determining the rate of product formation (G in FIG. 21). With respect to solid-based clinical chemistry assays, the present invention offers the only way to measure rate from a true time zero point since one can visualize and time the start of the reaction within milliseconds. This allows one to measure rates within the first few seconds of the assay, which is unique and useful. In addition, the width of the reaction interface band can be measured which can correlate with analyte concentration. Finally, all or a portion of the area of the interface band within a region of interest can be measured as a determination of total product formation (H in FIG. 21; FIG. 22). These parameters can be followed over time, or the same region can be compared among different samples to provide a relative measure of product development and thereby, analyte concentration.

The desired parameter may be measured by using any appropriate imaging device. Especially preferred are imaging devices that permit quantitation of the measured parameter by e.g., conversion of the measured values for the parameter into data suitable for processing by a computer. Examples of such devices include three-color CCD imaging cameras or three-chip imagers that may employ optics and a rotating filter wheel.

In another embodiment, a non-interfering component may be dried onto the fluid sample side of the bibulous material and be assayed at several points along the bibulous material as it is dissolved in the advancing sample fluid front to determine the presence of the sample at the interface. For example, a dye with an absorption spectra distinct from the product may be dried at the fluid sample side of the pad. Measurement of that dye at the fluid sample side of the reaction interface may be performed to determine the presence of fluid sample at the reaction site.

Figure 23:
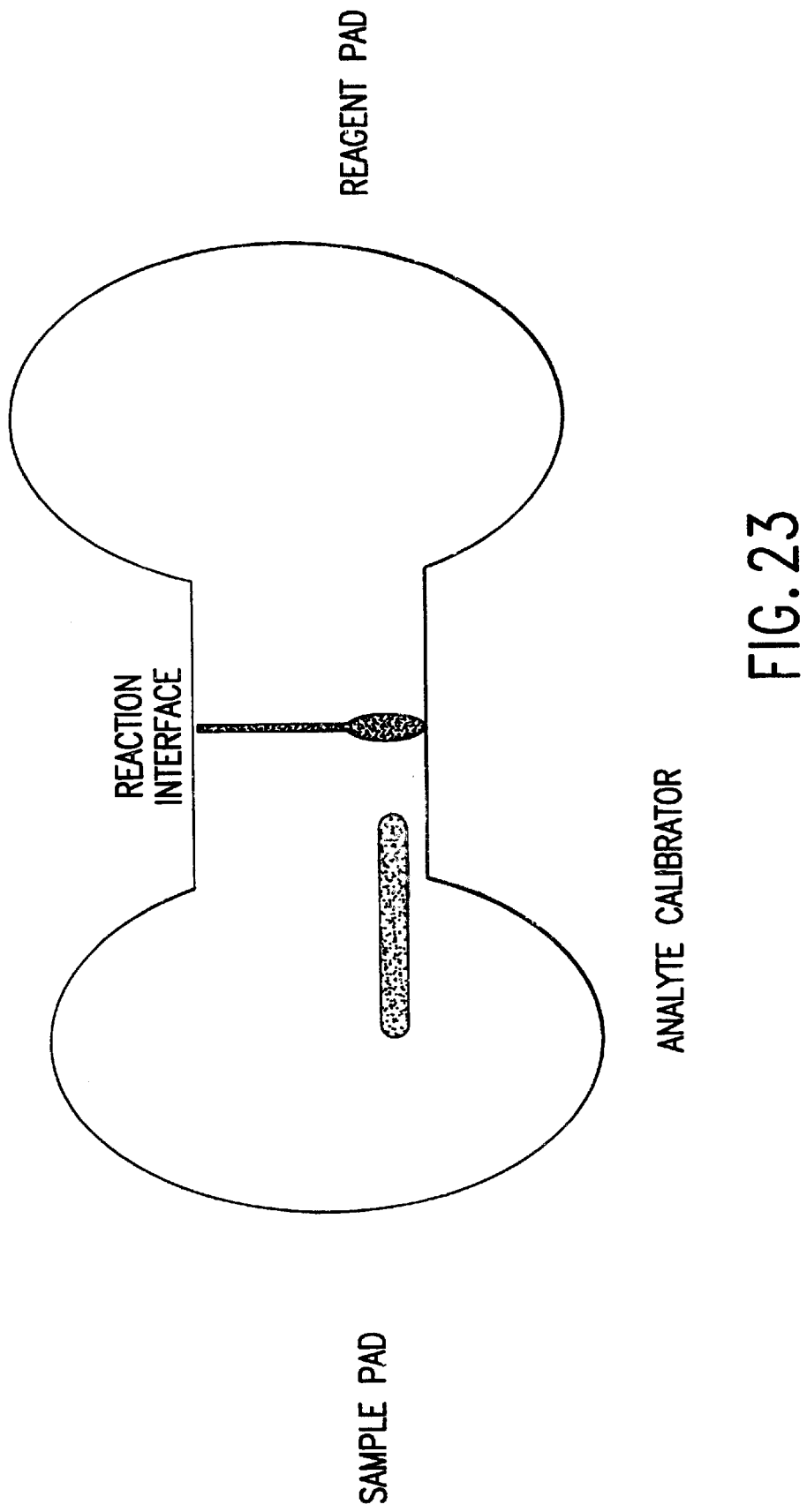
FIG. 23 is a schematic representation of the internal calibration procedure used in the methods and devices of the present invention, showing the application of the excess analyte near the sample pad in a strip format, and the subsequent formation of the analyte spot at the reaction product interface.
Figure 24:
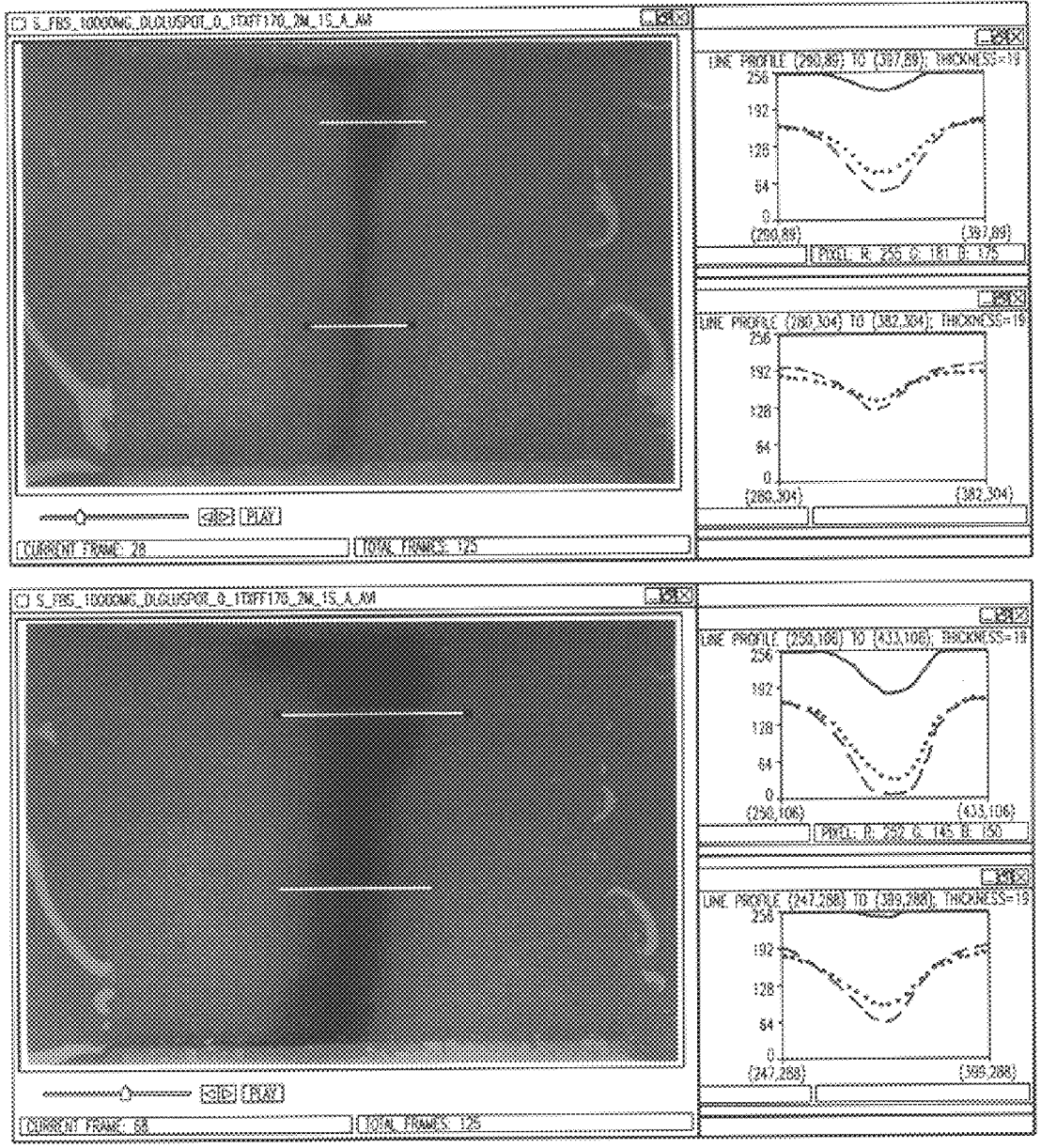
FIG. 24 is a digital color image of a glucose assay that demonstrates the internal calibration procedure of the present invention. The calibrated analyte (glucose) was applied at an excess concentration of about 100 mg/dl, and the glucose assay was run in accordance with the method of the present invention. The product at the reaction interface was measured at 20 seconds and 60 seconds after sample application.

In another embodiment, an amount of the analyte to be detected and/or measured may be dried at a spot on the bibulous material that is between the fluid sample application site and the liquid reagent application site. The analyte is reconstituted with a diluent, and the liquid reagent and the analyte flow toward one another as described above. The liquid reagent and the analyte meet and form a detectable calibration product. The calculation of the amount of the reaction product is assisted by a determination of the amount of reagent present at the reaction interface, which may be a function of the amount of the detectable calibration product. Generally, in the methods of the present invention directed to measurement of the concentration of an analyte, there is a great excess of reagent over analyte. However, to calibrate the amount of reagent at the reaction interface, the situation is reversed to produce an excess of analyte relative to reagent by spotting a relatively large amount of analyte onto the bibulous material, at a position in line with, but distinct from, the fluid sample application site (FIG. 23). The analyte may be applied in the form of a single high-concentration spot, but is more preferably applied as a stripe or slot of analyte (FIG. 23), since this permits the application of the same amount of analyte at a lower concentration, avoiding the possibility of problems associated with high concentrations of analyte, such as precipitation or crystallization of the analyte. The thus-applied analyte migrates with the sample toward the reagent application site and forms a large product spot at the reaction interface (FIG. 24). This spot may be measured in the same manner as the reaction product that is produced by the analyte sample. Deviations from expected values in the measurement of the calibration spot may signal the occurrence of any of a number of items that may influence reagent concentration, such as, for example, reagent degradation, reagent delivery difficulties, lack of reagent dissolution, precipitation of the reagent, and the like.

The above-described calibration method may also be used as a positive control method, to confirm the activity of the assay where a negative result is often expected. In this embodiment, a small amount of the analyte is applied to the bibulous material, and migrates toward the reagent application site. Formation of a detectable calibration product at the calibration interface provides evidence that the assay is working properly, and that any negative result is due to the absence of the analyte in the simultaneously-run liquid sample.

The following is an exemplary, non-comprehensive list of the analytes that can be identified with the present invention: alanine amino transferase (ALT) (enzyme substrate), albumin (dye binding), alkaline phosphatase (enzyme substrate), ammonia (enzymatic), amylase (enzyme substrate), aspartate amino transferase (AST) (enzyme substrate), total bilirubin (dye binding), calcium (dye binding), cholesterol (total) (enzymatic), creatine kinase (CK) (enzyme substrate), creatinine (dye binding), 2-glutamyl transferase (GGT) (enzyme substrate), glucose (enzymatic), lactate dehydrogenase (enzyme substrate), lipase (enzyme substrate), magnesium (dye binding), phosphorus (dye binding), protein (total) (dye binding), triglyceride (enzymatic), urea nitrogen (BUN) (enzymatic), and uric acid (enzymatic). The above referenced reaction types, enzyme substrate, dye bindings and enzymatic, can result in a chromogenic and/or ultraviolet reaction to identify the above listed analytes.

The following examples illustrate the use of the present invention to detect and quantify particular components in a fluid sample. These examples are provided for illustration, and are not intended to be limiting. The person of skill will realize that the principles and techniques illustrated may be applied to detect a variety of analytes in a variety of fluid samples.

EXAMPLE 1

This example illustrates how a device of the present invention was used to determine the presence and concentration (246 mg/dl) of glucose in a sample of whole blood.

A HEMOSEP L® membrane was affixed to an adhesive plastic backing and cut into 4 mm×25 mm strips. Trinder reagent (15 $\mu$l) (Sigma Chemical Co., St. Louis, Mo.) containing glucose oxidase (15,000 $\mu$/L), 4-aminoantypyrine (0.5 mM), p-hydroxybenzene sulfonate (20 mM) and peroxidase (10,000 $\mu$/L) at pH approximately 7.0 was dried onto one end of each test strip, comprising about one-half of the total strip area. This was accomplished by simultaneously dispensing 10 $\mu$l of water to one end of the strip (the fluid sample side) and 10 $\mu$l of Trinder reagent (at 5×concentration) to the other end of the strip (the diluent solution side). The strip was then air dried for 1 hour at room temperature.

After drying, 15 $\mu$l of water was added to the outer end of the diluent solution side of the strip at the diluent solution application site and 15 $\mu$l of whole blood was added simultaneously to the outer end of the fluid sample side of the strip at the fluid sample application site. The two liquids flowed towards each other, eventually yielding four distinct bands on the strip: a red blood cell band, a plasma band, a red/brown quinoneimine dye reaction product band (the reaction interface), and a band of unreacted Trinder reagent. As shown in FIGS. 4A–4F, the quinoneimine dye colored product interface band continued to develop over several minutes, with its rate of development and final color intensity being proportional to the starting concentration of glucose in the sample.

EXAMPLE 2

This example illustrates how the present invention was applied to detect and quantify calcium in fetal calf serum.

Three polyethersulfone membranes were prepared as described in Example 1 and washed with 50 $\mu$l of dilute HCl at pH 2.0. An example of a suitable polyethersulfone membrane for use in the present invention is a SUPOR® membrane (Pall-Gelman, Port Washington, N.Y.). The person of ordinary skill will realize that other porous membranes with similar characteristics may also be applied to the present invention. Fifteen microliters of fetal calf serum containing 6.8, 13 and 18.6 mg/dl of calcium was added to the fluid sample side of each strip at the fluid sample application site while simultaneously adding 15 $\mu$l of acidified Arsenazo III red/purple dye solution (Sigma Chemical Co., St. Louis, Mo.; catalog no. 588, prepared according to the manufacturer's instructions) to the diluent solution side of the strip at the diluent solution application site. In each case, the two liquids flowed towards each other and upon meeting formed a discrete interface. The blue reaction product, calcium-arsenazo III, developed at the product interface. As shown in FIGS. 5A–5I, both the time for color development and final intensity of blue color were proportional to the starting concentration of calcium in the fluid samples.

EXAMPLE 3

In this example, 1.2 g/dl and 1.9 g/dl concentrations of albumin in fetal calf serum were tested with the present invention using bromocresol green dye after adjustment to pH 5.5.

Figure 7:
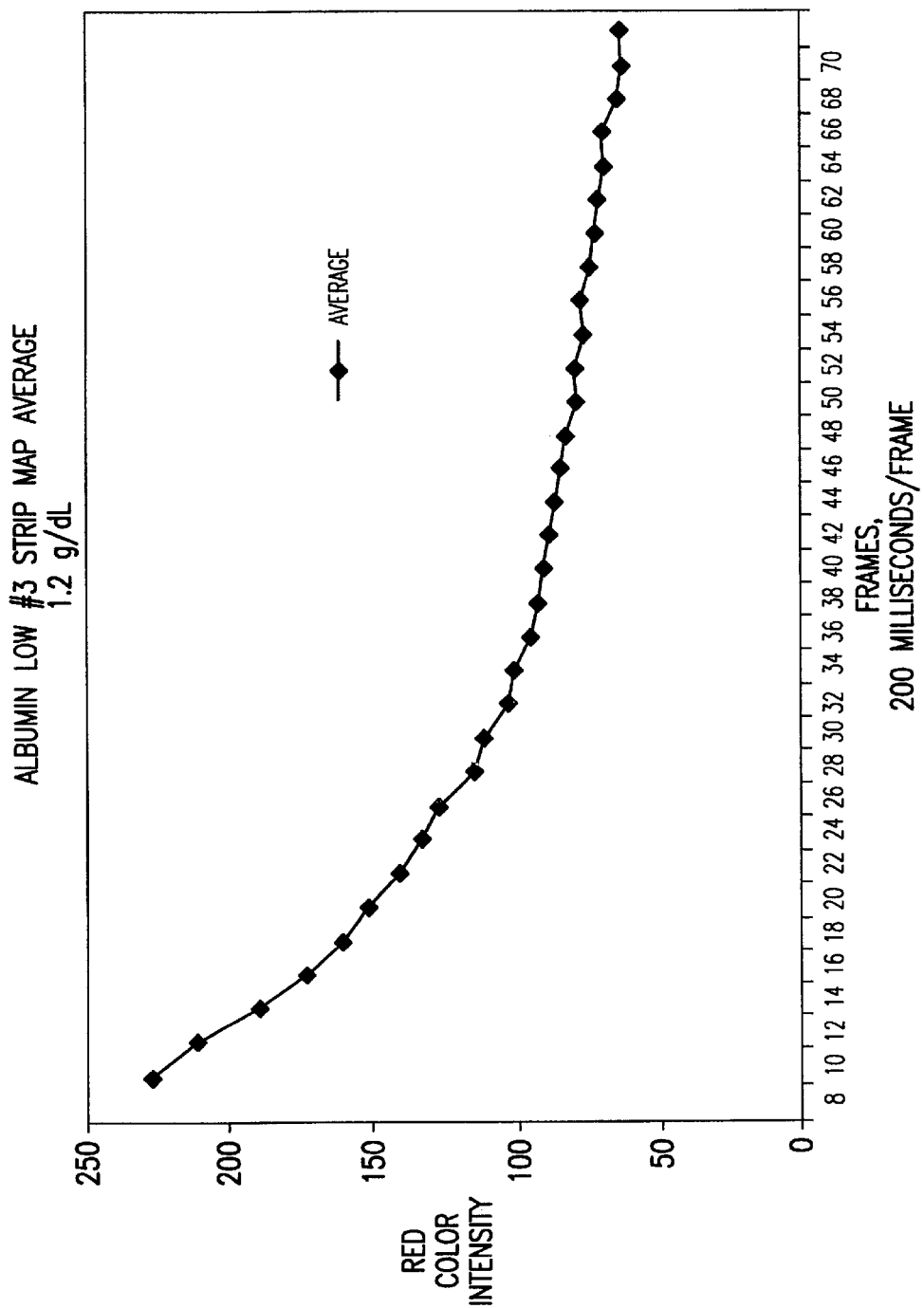
FIG. 7 is a numerical tabulation of color intensity versus time for six independently read reflective values of a reaction interface, and the average value and slope of sample having an albumin concentration of 1.2 g/dl based on an assay run with the present invention.
Figure 8:
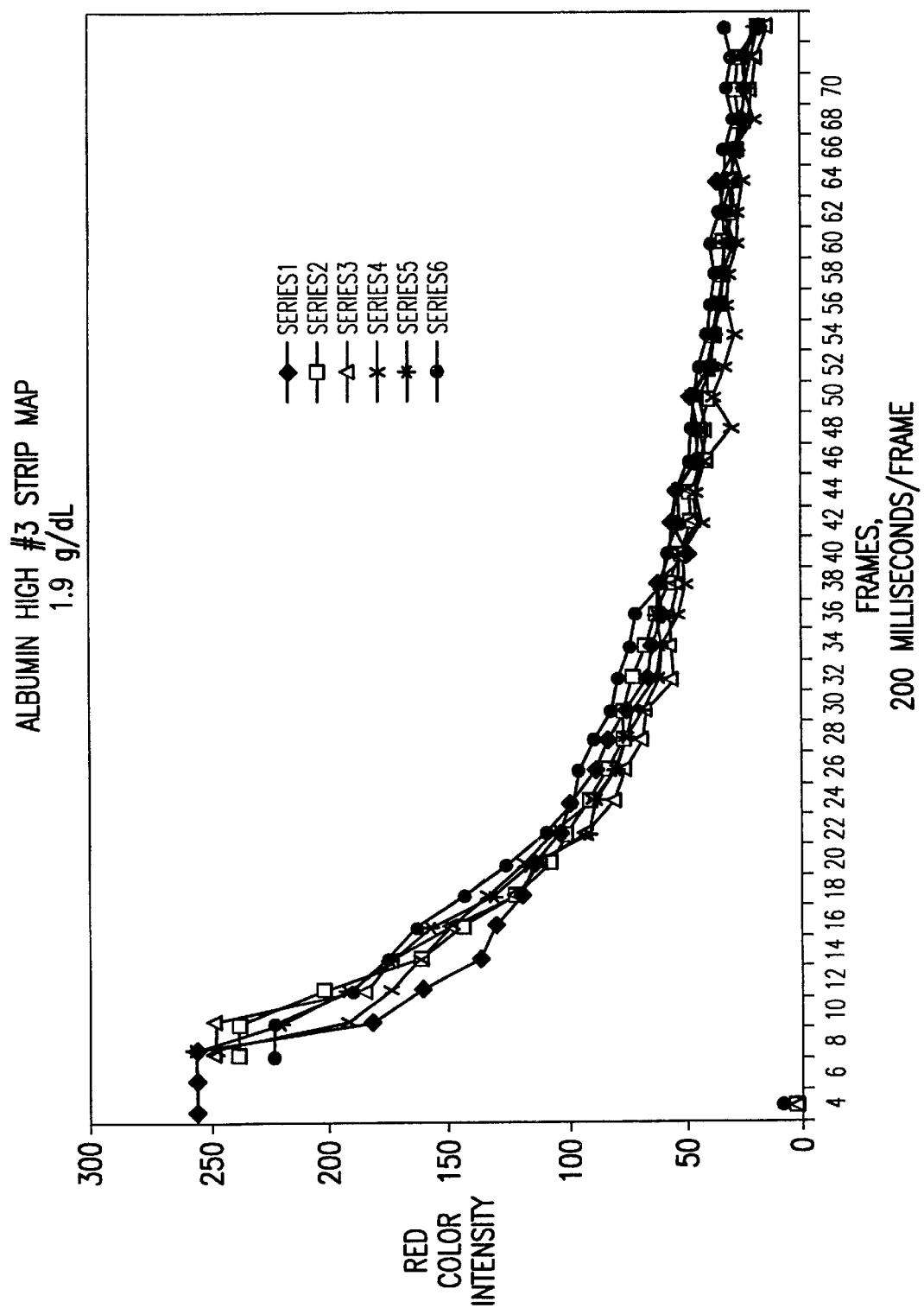
FIG. 8 is a graph of color intensity versus time for six independently read reflective values of a reaction interface from a sample having an albumin concentration of 1.9 g/dl based on an assay run with the present invention.
Figure 9:
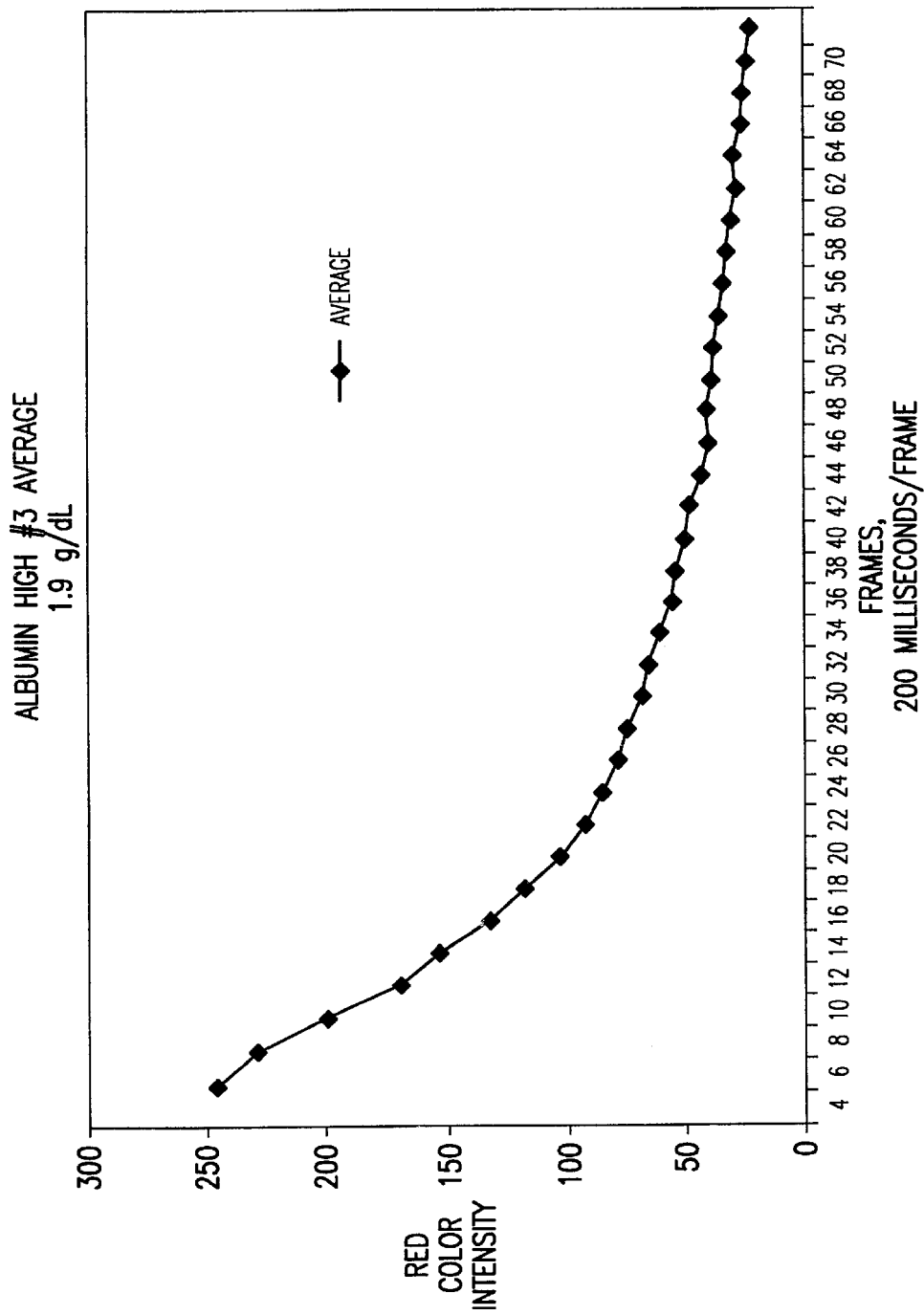
FIG. 9 is a numerical tabulation of color intensity versus time for six independently read reflective values of a reaction interface, and the average value and slope of a sample having an albumin concentration of 1.9 g/dl based on an assay run with the present invention.
Figure 10:
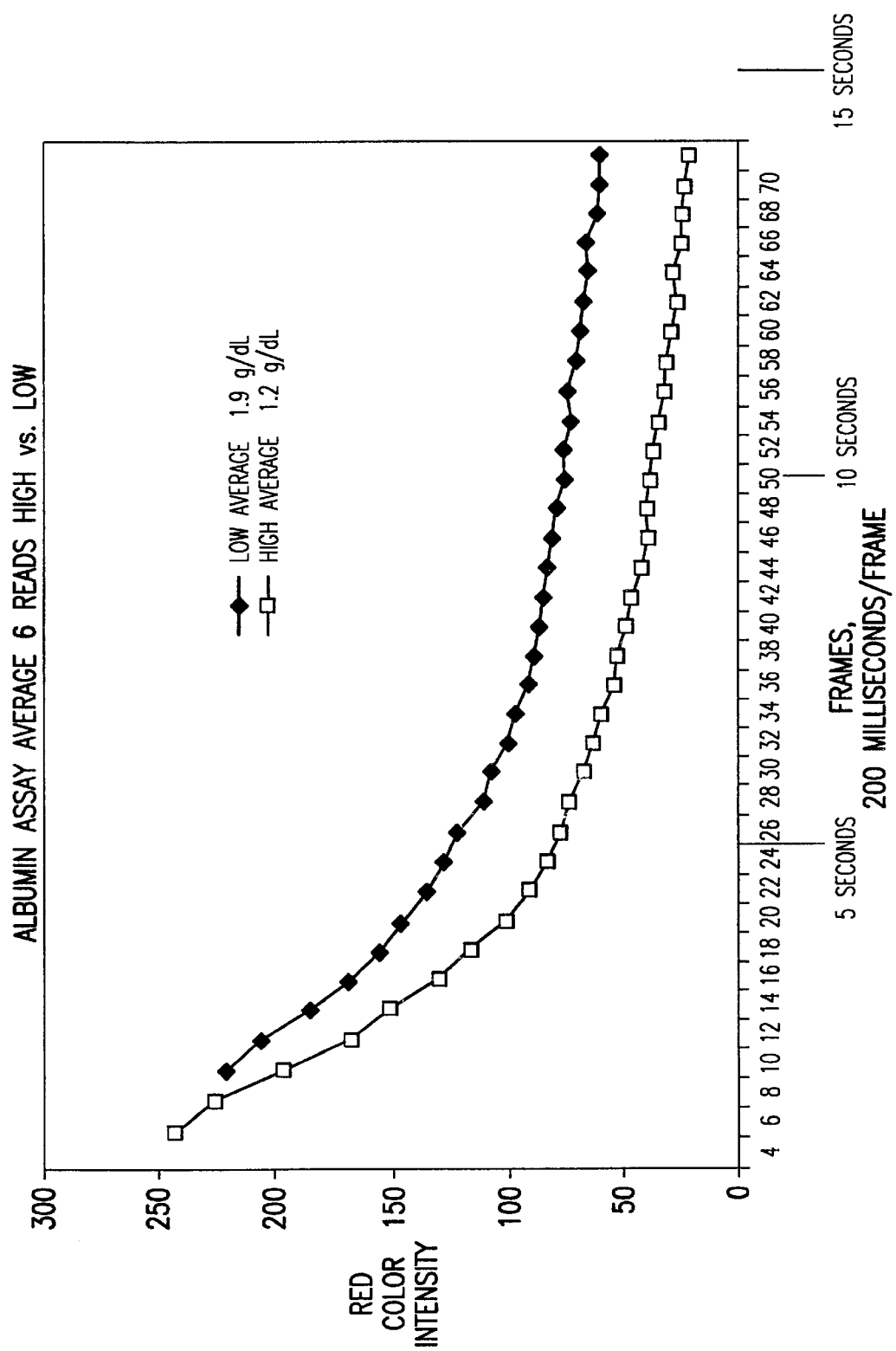
FIG. 10 is a graph of color intensity versus time for the averaged red reflective values of samples having albumin concentrations of 1.2 g/dl and 1.9 g/dl based on an assay run with the present invention and read over 15 seconds.
Figure 11:
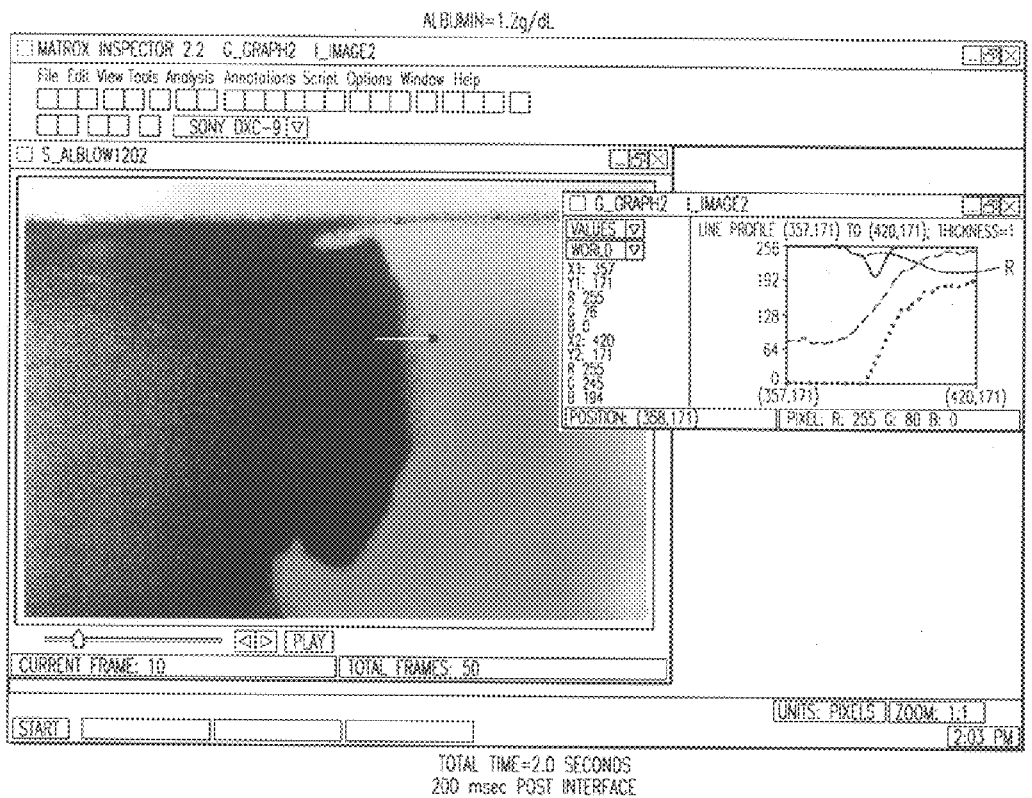
FIG. 11 is a digital color image of an assay run with the present invention of a sample having an albumin concentration of 1.2 g/dl within 200 mseconds of interface formation and 2.0 seconds after sample application, as well as the associated color absorption graph for a selected portion of the digital color image.
Figure 12:
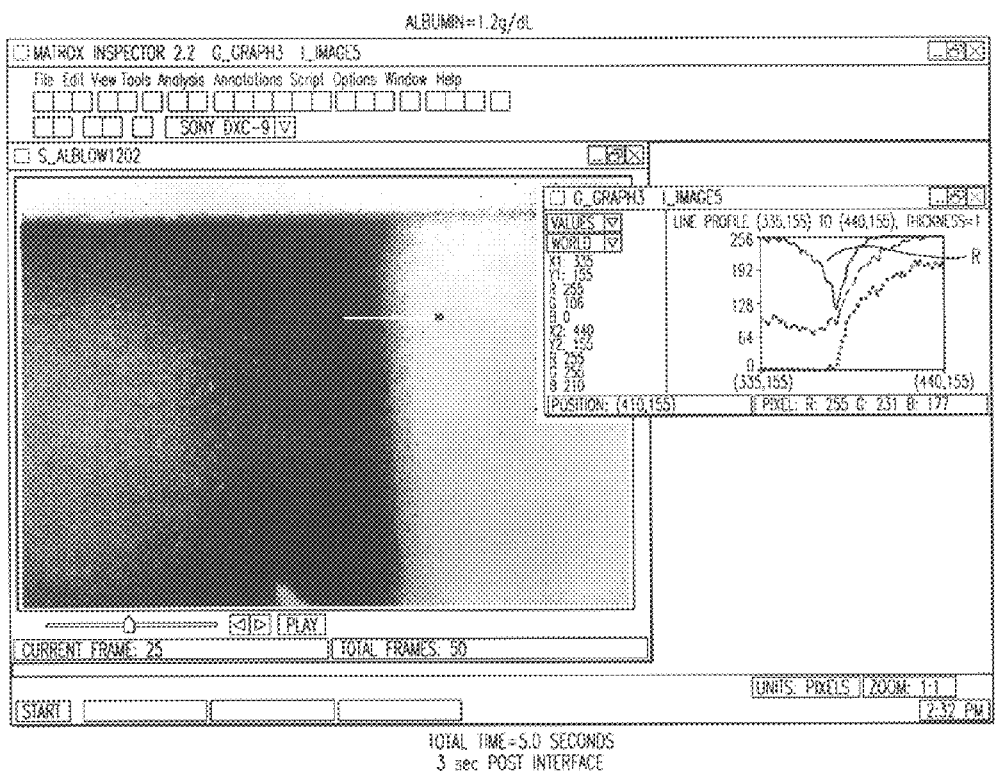
FIG. 12 is a digital color image of an assay run with the present invention of a sample having an albumin concentration of 1.2 g/dl at three (3) seconds after interface formation and five (5) seconds after sample application, as well as the associated color absorption graph for a selected portion of the digital color image.
Figure 13:
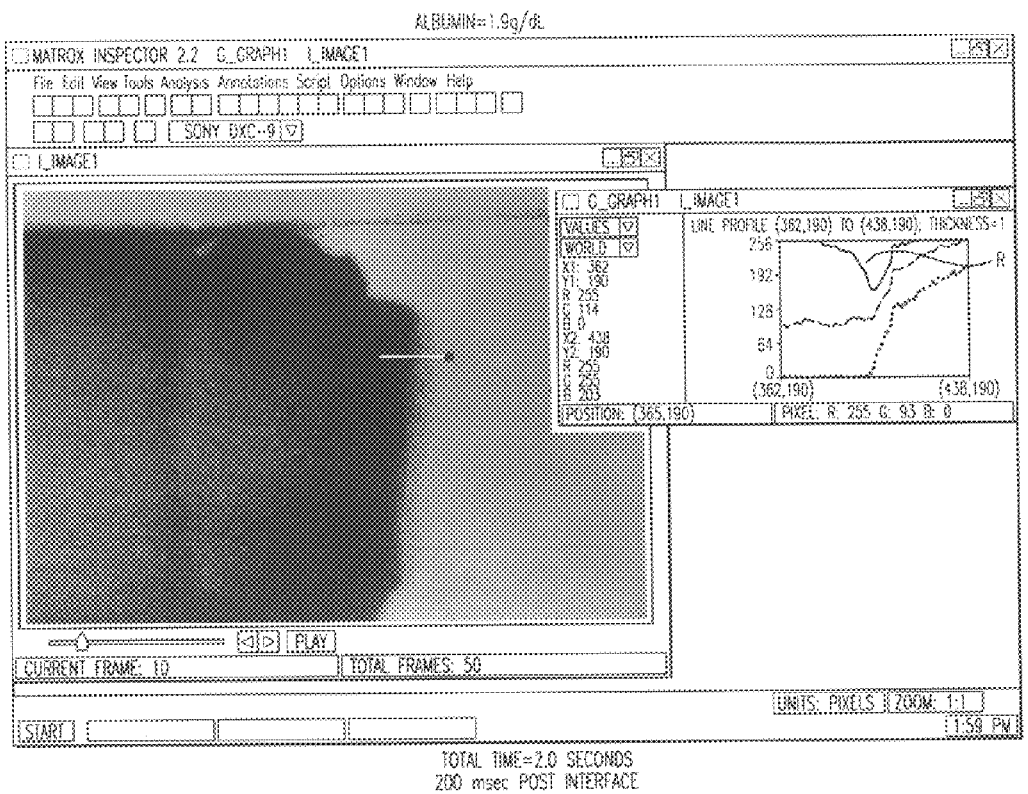
FIG. 13 is a digital color image of an assay run with the present invention of a sample having an albumin concentration of 1.9 g/dl within 200 mseconds of interface formation and 2.0 seconds after sample application, as well as the associated color absorption graph for a selected portion of the digital color image.
Figure 14:
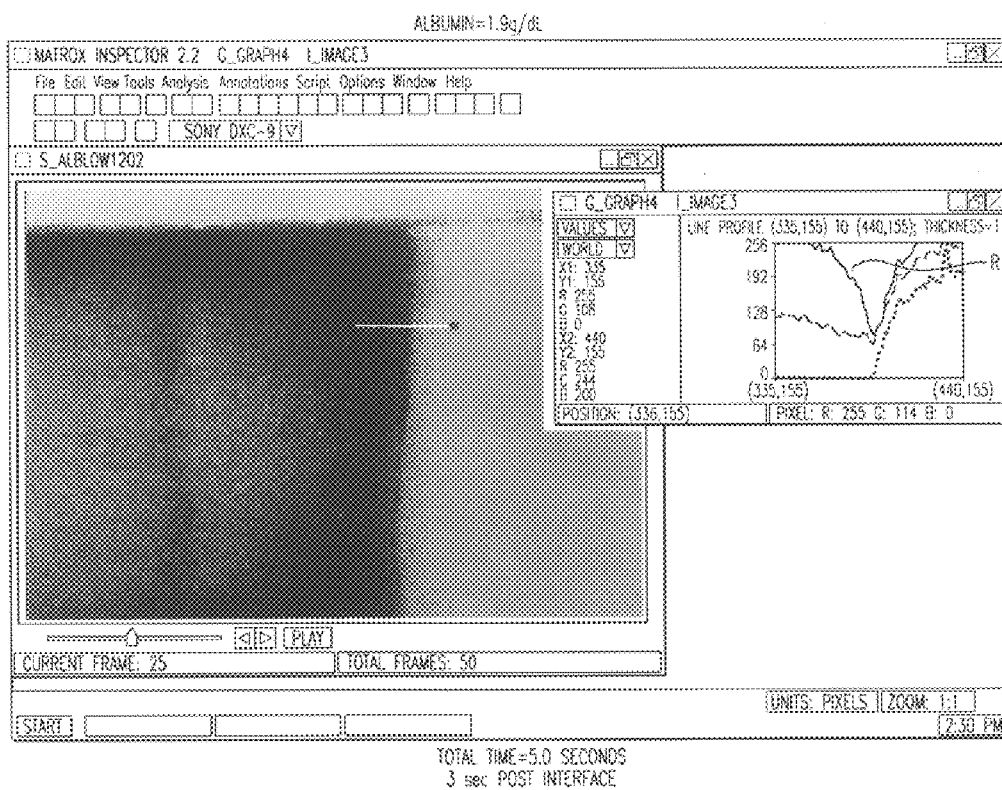
FIG. 14 is a digital color image of an assay run with the present invention of a sample having an albumin concentration of 1.9 g/dl at three (3) seconds after interface formation and five (5) seconds after sample application, as well as the associated color absorption graph for a selected portion of the digital color image.
Figure 15:
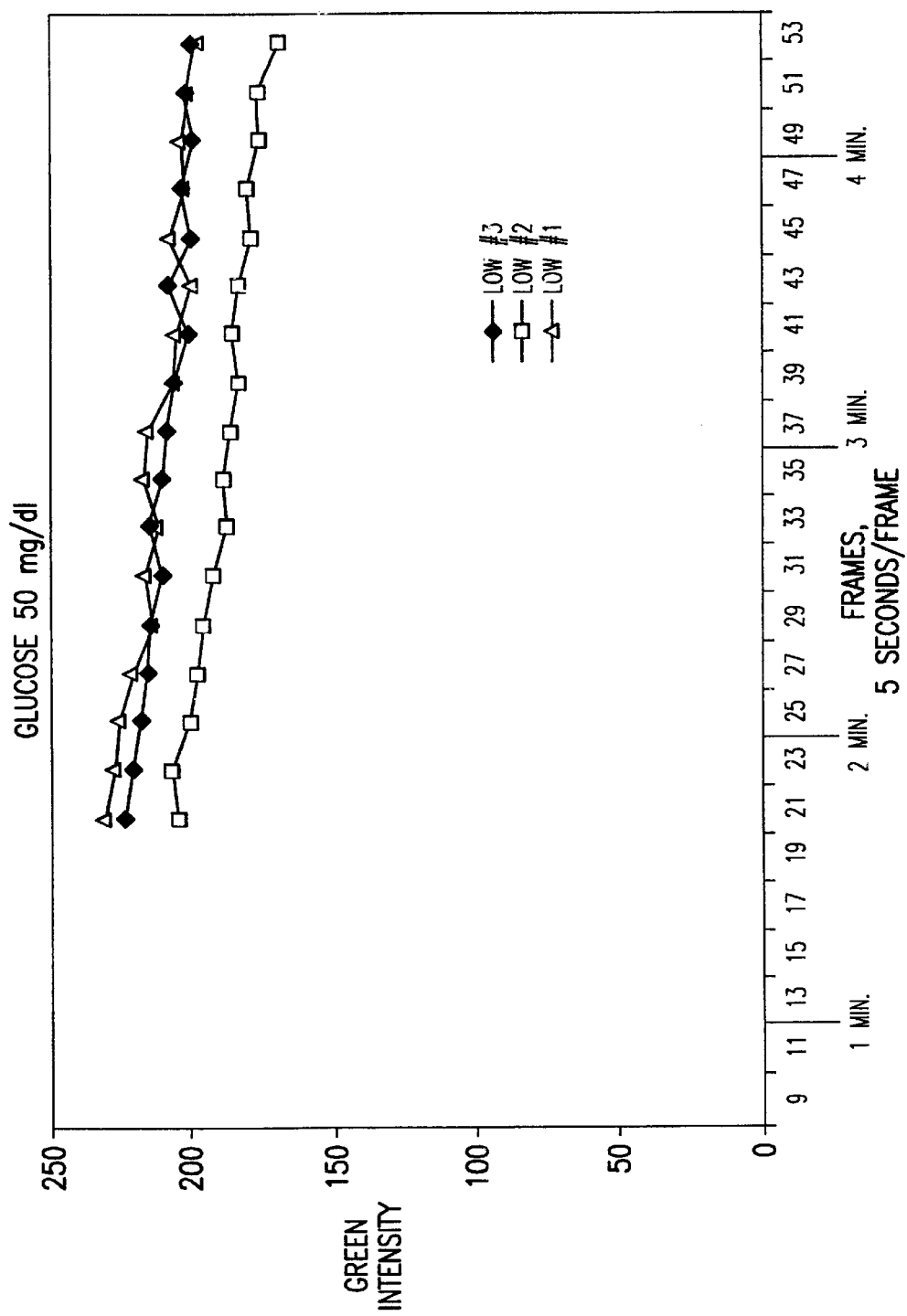
FIG. 15 is a graph of color intensity versus time for three different devices reading a sample having a glucose concentration of 50 mg/dl based on an assay run with the present invention.
Figure 16:
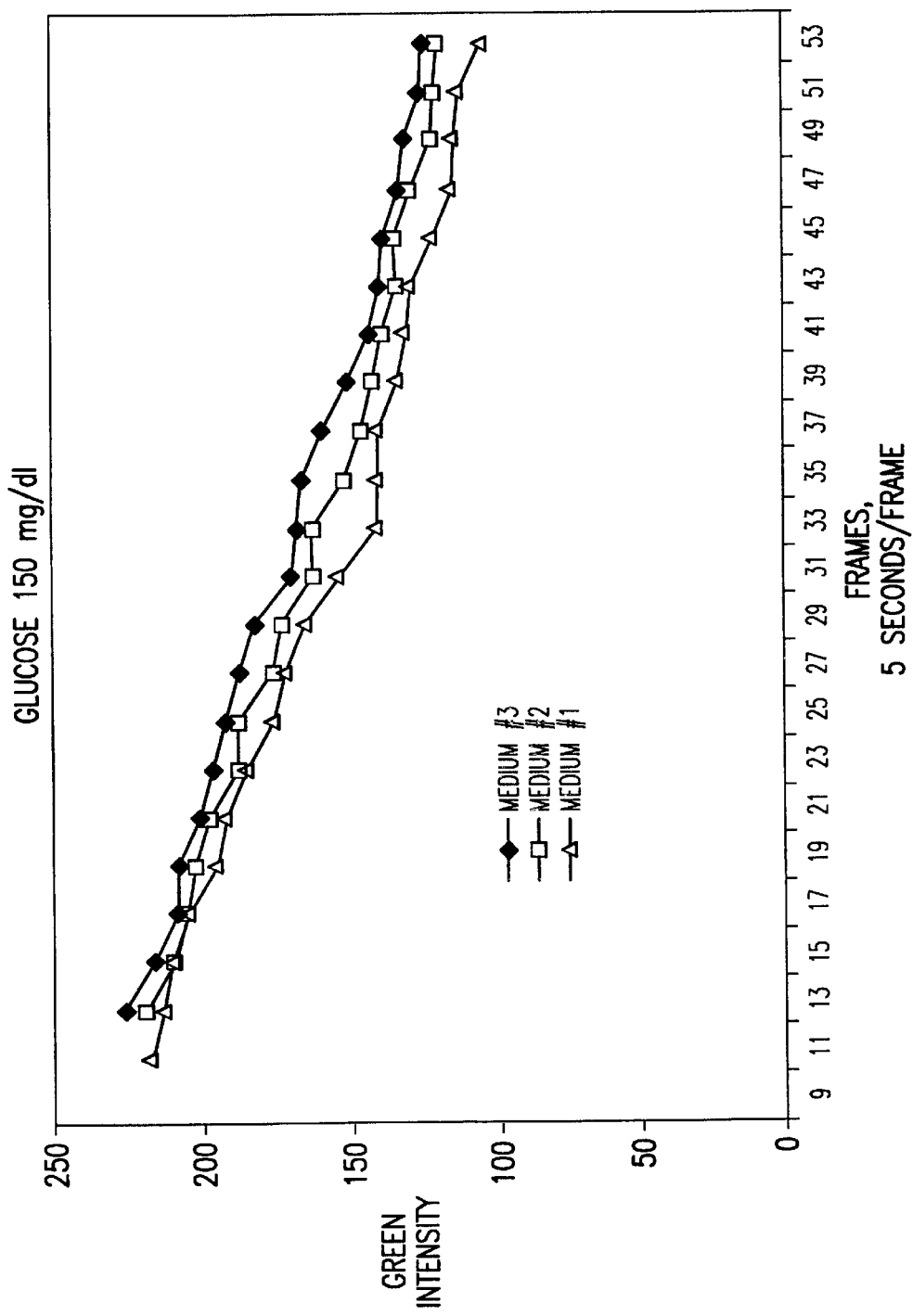
FIG. 16 is a graph of color intensity versus time for three different devices reading a sample having a glucose concentration of 150 mg/dl based on an assay run with the present invention.
Figure 17:
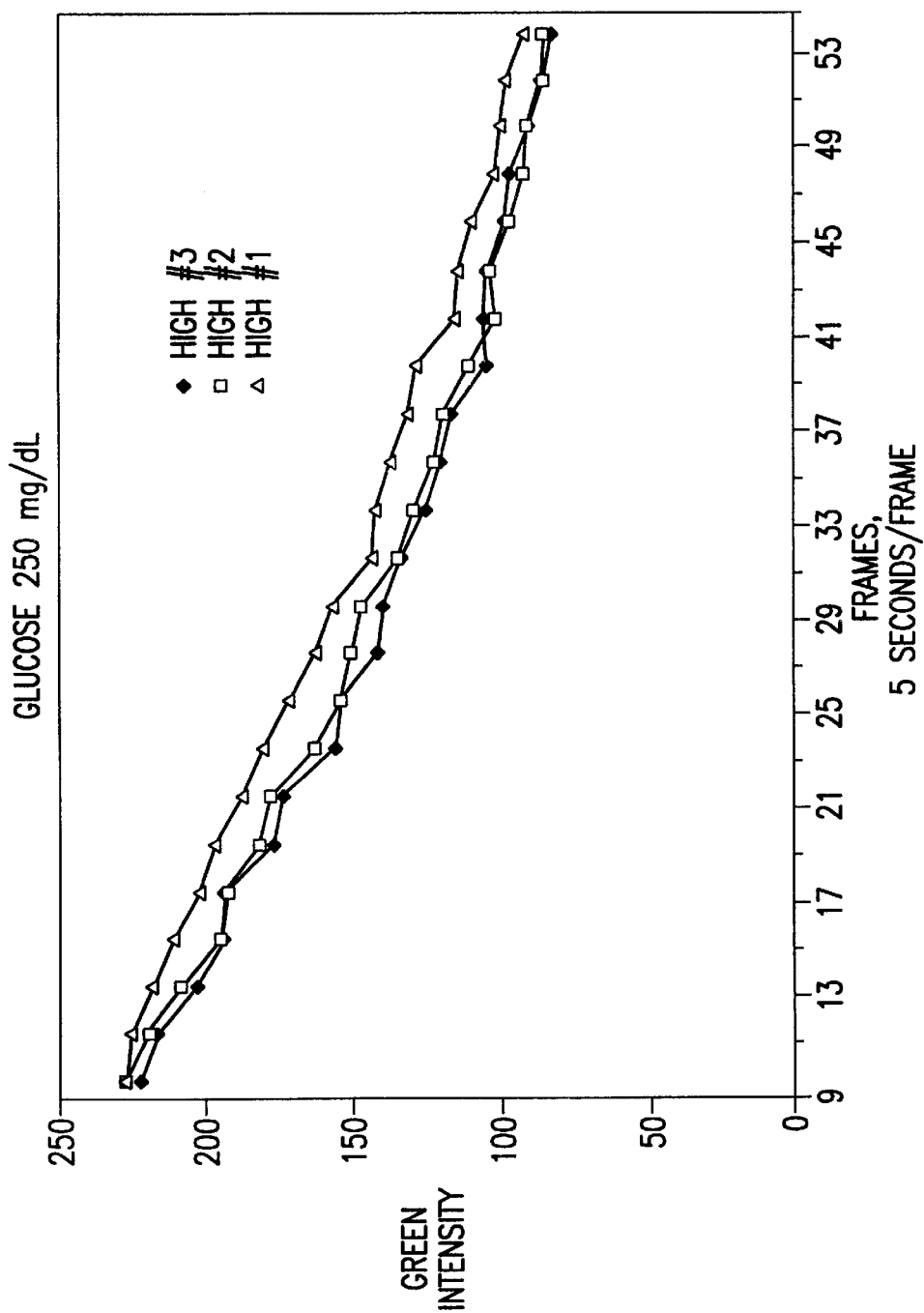
FIG. 17 is a graph of color intensity versus time for three different devices reading a sample having a glucose concentration of 250 mg/dl based on an assay run with the present invention.
Figure 18:
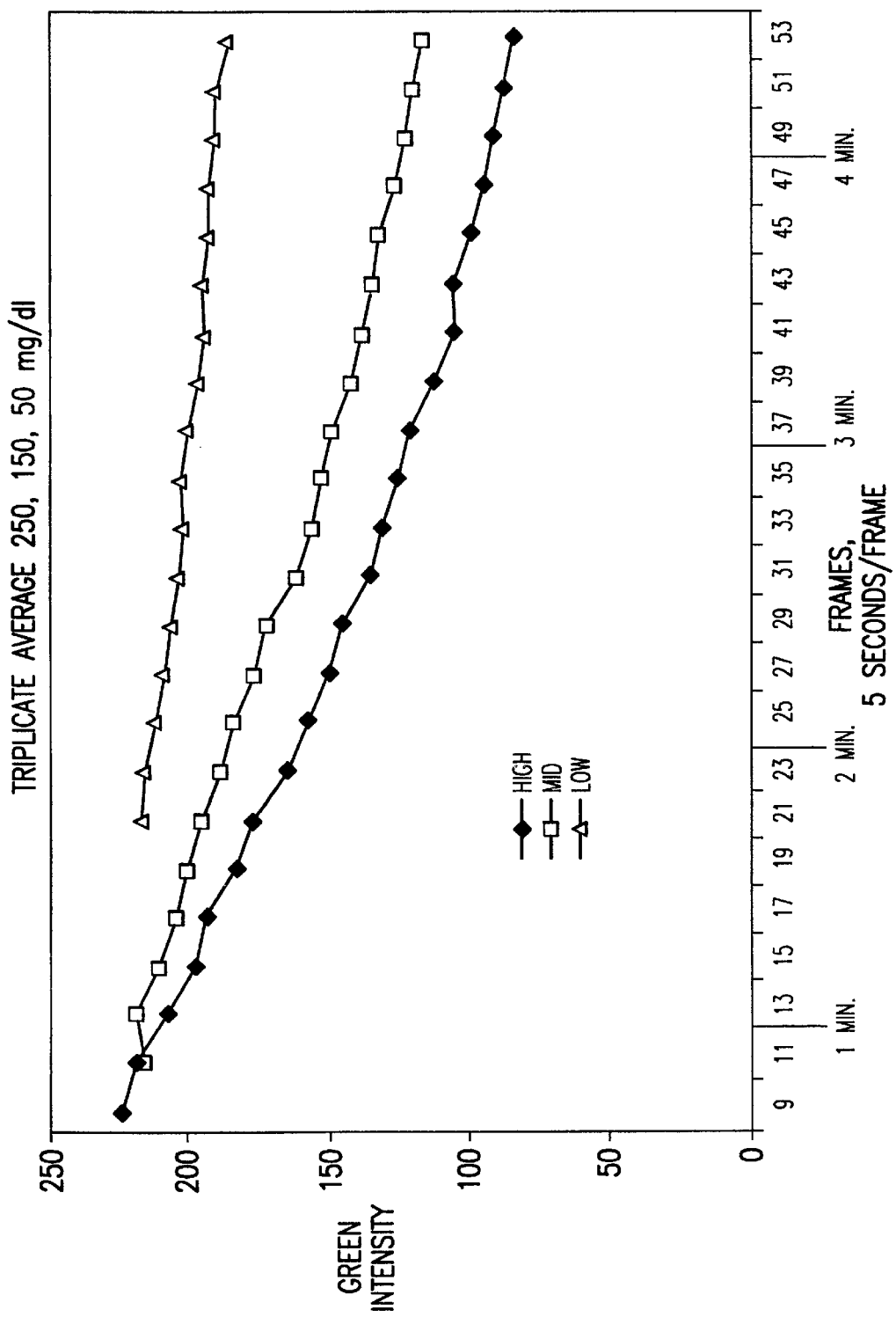
FIG. 18 is a graph of color intensity versus time for the average value of samples having a glucose concentration of 50 mg/dl, 150 mg/dl and 250 mg/dl based on an assay run with the present invention and read over 4.5 minutes.

A HEMOSEP L® membrane was affixed to an adhesive plastic backing and cut into 4 mm×25 mm strips. BCG reagent (15 µl; Sigma Chemical Co., St. Louis, Mo.; catalog no. 631, prepared according to the manufacturer's instructions, except that a 10×concentrated solution of the reagent was used) was added to one end of each test strip, comprising about one-half of the total strip area. Serum (15 µl) was added simultaneously to the outer end of the fluid sample side of the strip at the fluid sample application site. The two liquids flowed towards each other, eventually yielding three distinct bands on the strip: a serum band, a reaction product band (the reaction interface), including a dye/albumin complex, and a band of unreacted BCG reagent. FIG. 5, 7 and 10 are graphical representations, and FIGS. 5 and 9 are numerical representations, of the color intensity of the reaction product versus time for both of the 1.2 g/dl and 1.9 g/dl samples. These graphs show that the assay performed in accordance with the subject invention produces a substantial color intensity within five (5) seconds from application of the sample to the test strip of the present invention which is proportional to the original analyte concentration based on slope and final color intensity.

FIGS. 11 through 14 are digital photographs of the 1.2 g/dl and 1.9 g/dl test strips at 200 milliseconds (2.0 seconds after sample application to the test strip) and at 3.0 seconds after interface formation (5.0 seconds after sample application to the test strip). These digital images were recorded with a Sony Progressive 3CCD camera and the digital data was loaded to a Gateway PC, where a selected row of pixels of the images was analyzed using the INSPECTOR color absorption software by Matrox. Comparing FIG. 11 with FIG. 12 for the 1.2 g/dl sample and FIG. 13 with FIG. 14 for the 1.9 g/dl sample, a large increase in red absorption (green color) occurred in under three (3) seconds, as shown by line "R" in FIGS. 11 through 14, which represents the increase in red absorption (higher green color) across the reaction interface. In general, throughout this application an increase in absorption at a given color is reflected as a downward deflection in the color graph. Thus, the test protocol of the present invention produces an ascertainable reaction at a reaction rate such that the test can be performed in five (5) seconds from sample addition and in three (3) seconds after interface formation.

EXAMPLE 4

This is another example using the protocol of Example 1, and illustrating how a device of the present invention was used to determine the presence and concentration of glucose in a sample of whole blood. In this example, 50 mg/dl, 150 mg/dl and 250 mg/dl samples were used.

A HEMOSEP L® membrane was affixed to an adhesive plastic backing and cut into 4 mm×25 mm strips. 15 µl Trinder reagent (Sigma Chemical Co., St. Louis, Mo., catalog number 315, prepared according the manufacturer's instructions except a 5×concentration reagent solution was used) containing glucose oxidase (15,000 u/L), 4-aminoantypyrine (0.5 mM), p-hydroxybenzene sulfonate (20 mM) and peroxidase (10,000 u/L) at pH approximately 7.0 was added to one end of each test strip, comprising about one-half of the total strip area. Serum (15 µl) was added simultaneously to the outer end of the fluid sample side of the strip at the fluid sample application site. The two liquids flowed towards each other, eventually yielding three distinct bands on the strip: a serum band, a red/brown quinoneimine dye reaction product band (the reaction interface), and a band of unreacted Trinder reagent. FIGS. 15 through 18 show the rate of development of the quinoneimine dye product. These graphs show that the assay performed in accordance with the subject invention produces a substantial color intensity within 2–4 minutes from application of the sample to the test strip of the present invention.

EXAMPLE 5

This is another example using the protocol of Example 2, and illustrating how the present invention was applied to detect and quantify calcium in fetal calf serum. In this example, 9.3 mg/dl and 13 mg/dl samples were used.

Figure 19:
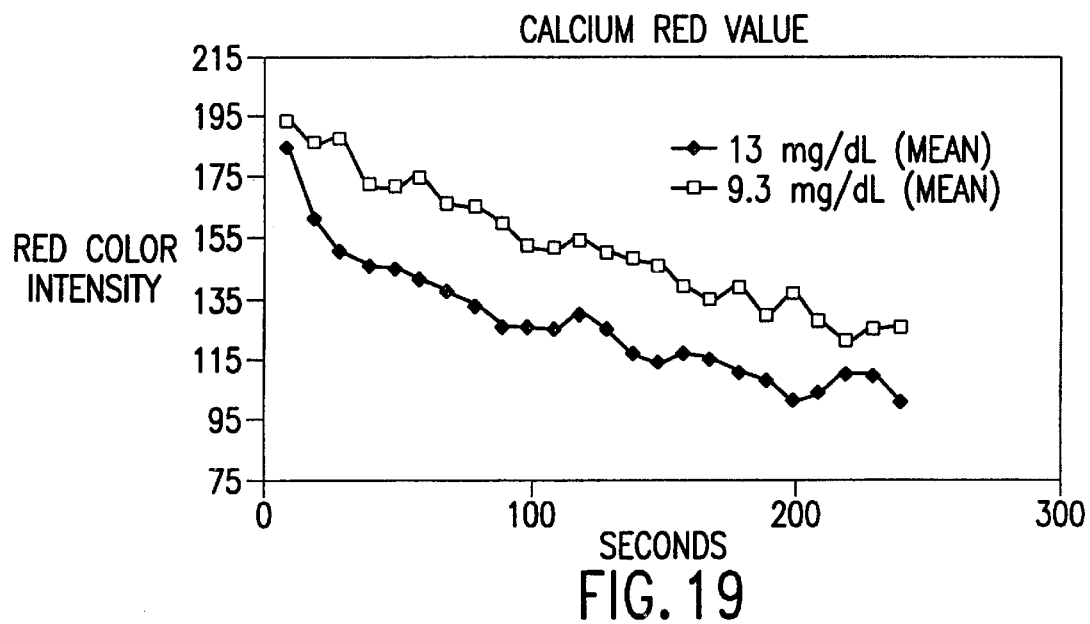
FIG. 19 is a graph of color intensity versus time for samples having calcium concentrations of 9.3 mg/dl and 13 mg/dl based on an assay run with the present invention.
Figure 20:
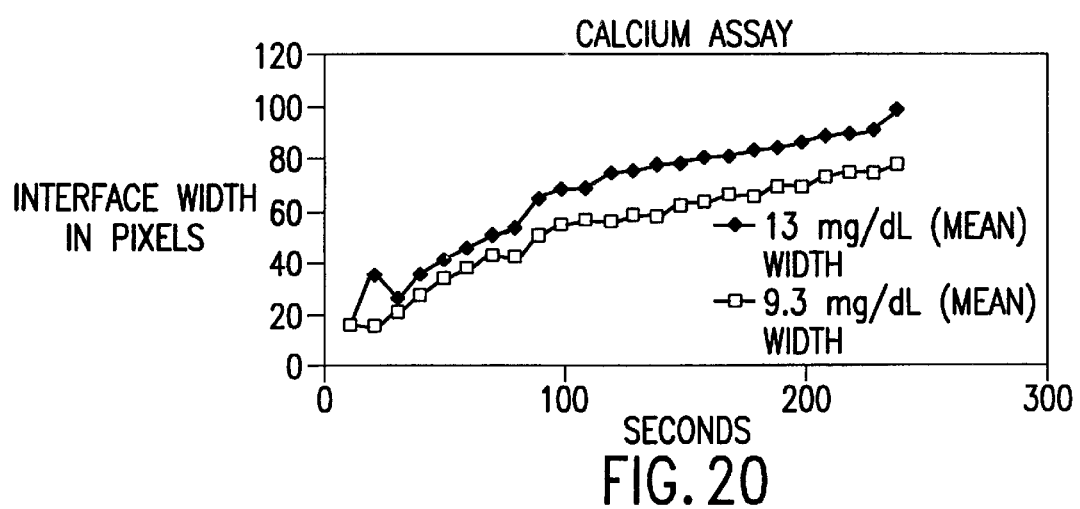
FIG. 20 is a graph of interface width versus time for samples having calcium concentrations of 9.3 mg/dl and 13 mg/dl based on an assay run with the present invention.

Polyethersulfone membranes were prepared as described in Example 1 and washed with 50 µl of dilute HCl at pH 2.0. Fifteen microliters of fetal calf serum containing 9.3 mg/dl and 13 mg/dl of calcium was added to the fluid sample side of each strip at the fluid sample application site while simultaneously adding 15 µl of acidified Arsenazo III red/purple dye solution to the diluent solution side of the strip at the diluent solution application site. In each case, the two liquids flowed towards each other and upon meeting formed a discrete interface. The blue reaction product, calcium-arsenazo III, developed at the interface. Referring to FIGS. 19 and 20, which show graphical and numerical representations of this example, FIG. 19 shows that the assay performed in accordance with the subject invention produces a substantial color intensity within one minute from application of the sample to the test strip of the present invention.

FIG. 20 shows the relative stability of the interface width over time. The interface width approximately doubles from 100 seconds to 250+ seconds.

EXAMPLE 6

This example illustrates how the present invention was applied to detect and quantify total alkaline phosphatase in fetal calf serum. In this example, serial dilutions of alkaline phosphatase over a 10-fold range in concentrations were used.

Figure 25:
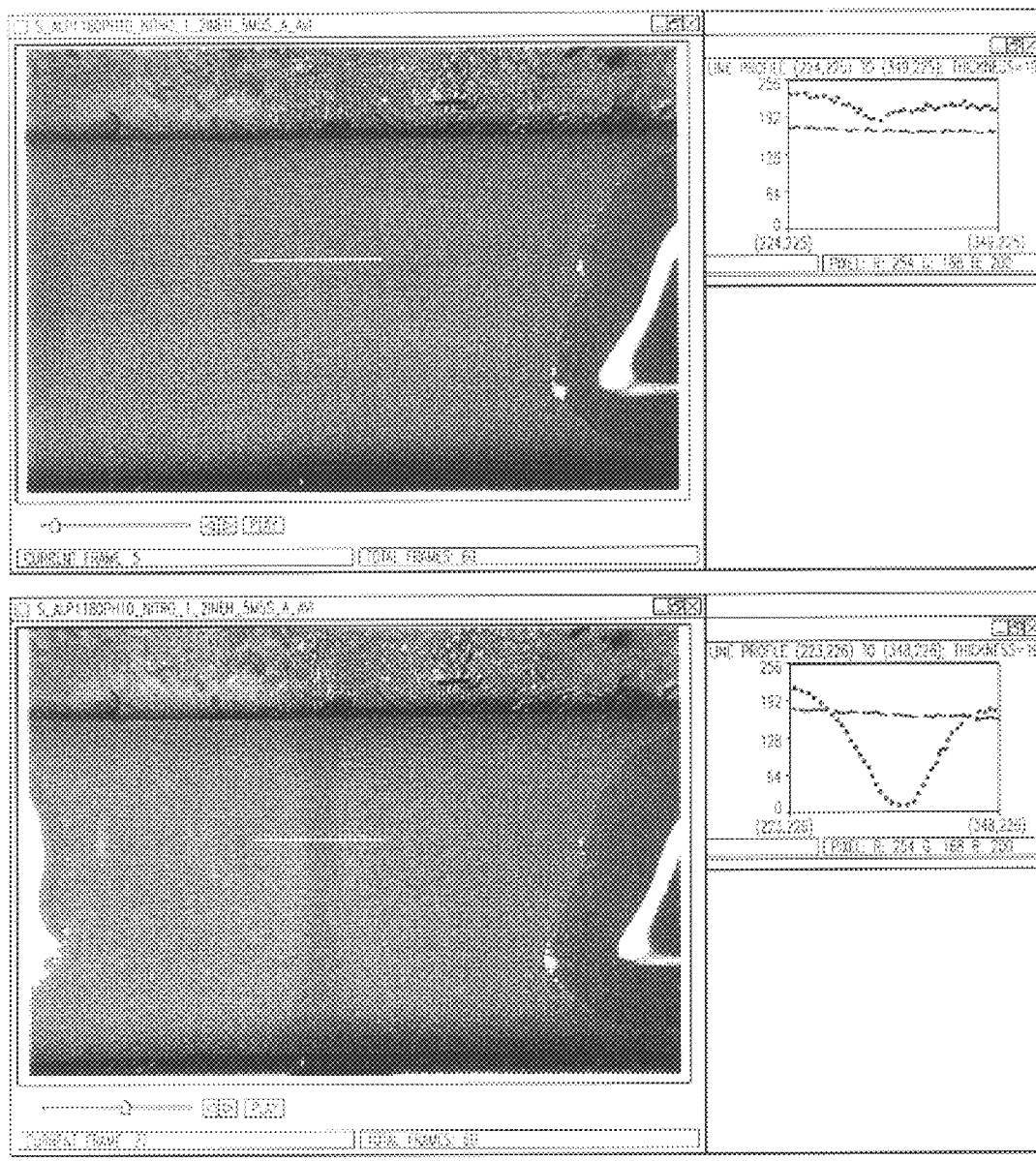
FIG. 25 is a digital color image of an alkaline phosphatase assay run in accordance with the method of the present invention at 15 seconds and 120 seconds after sample application, as well as the associated color absorption graph for a selected portion of the digital color image at each time point.

Nitrocellulose membrane strips were washed with dilute NaOH at pH 10. Fifteen microliters of fetal calf serum containing various dilutions of alkaline phosphatase was applied to the fluid sample side of the membrane strip at the fluid sample application site while simultaneously adding 15 µl of alkaline phosphatase reagent (Sigma Catalog No. 245, prepared according to the manufacturer's instructions except a 2×concentrated reagent solution was used) to the diluent solution side of the strip at the diluent solution application site. In each case, the two liquids flowed towards each other and upon meeting formed a discrete interface. The reaction product, p-nitrophenol, developed at the product interface. FIG. 25 is a digital photograph of one of the test strips, showing product formation at 15 seconds and 120 seconds after sample application to the test strip. These digital images were recorded as described for Example 3. FIG. 25 shows that the assay performed in accordance with the subject invention produces a detectable color intensity within 15 seconds from application of the sample to the test strip of the present invention, and a substantial color intensity by 120 seconds.

EXAMPLE 7

This example shows how the present invention was applied to detect and quantify total bilirubin in fetal calf serum. In this example, 0.65 mg/dl, 2.55 mg/dl, 4.73 mg/dl, 9.39 mg/dl, and 19.57 mg/dl samples were used.

Figure 26:
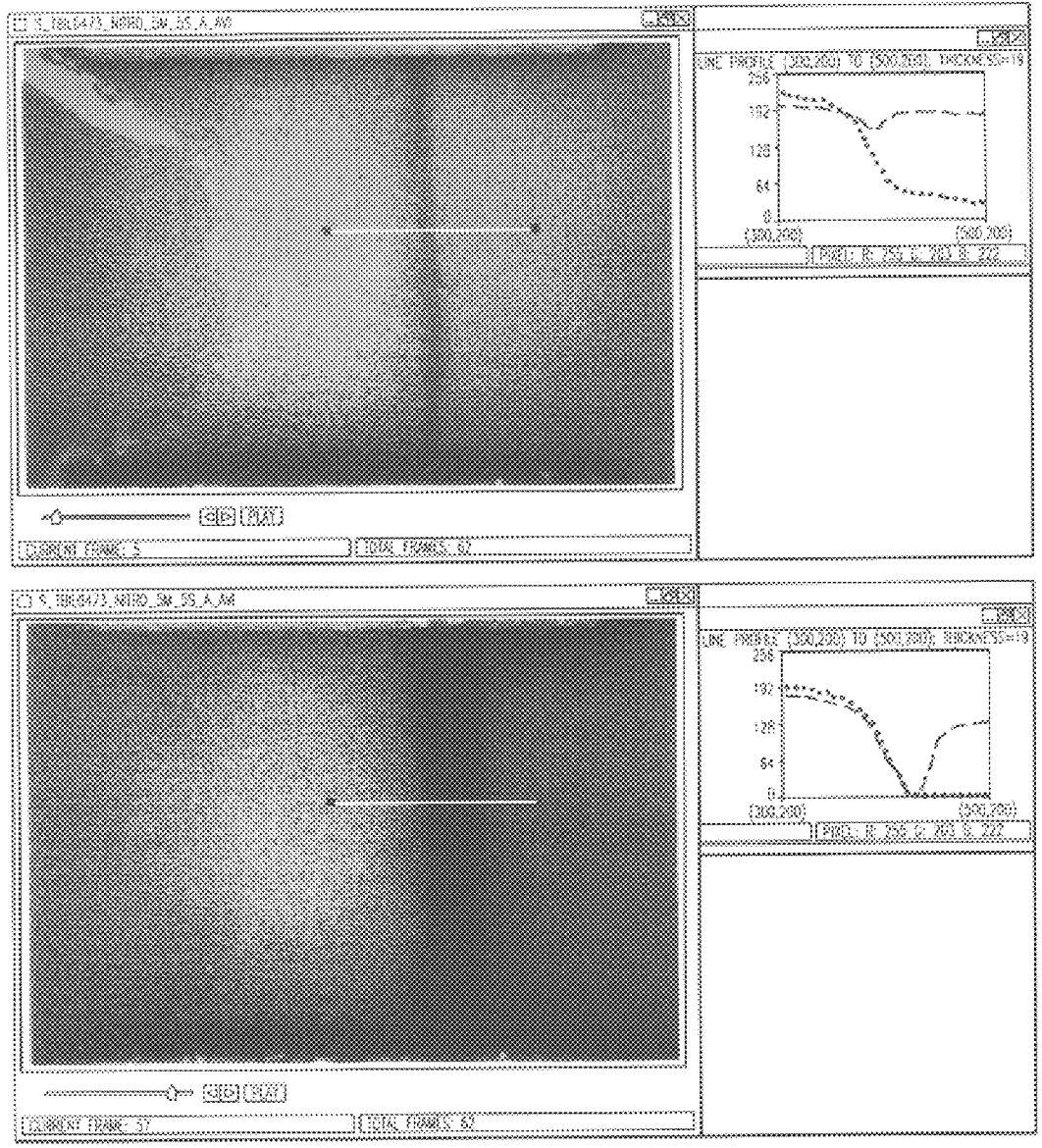
FIG. 26 is a digital color image of an assay for total bilirubin run in accordance with the method of the present invention at a concentration of 4.73 mg/dl total bilirubin, and measured at 15 seconds and 275 seconds after sample application, as well as the associated color absorption graph for a selected portion of the digital color image at each time point.

Polyethersulfone membranes were prepared as described in Example 1 and washed with water at pH 7.0. Fifteen microliters of a commercial standard solution containing 0.65 mg/dl, 2.55 mg/dl, 4.73 mg/dl, 9.39 mg/dl, or 19.57 mg/dl of bilirubin was added to the fluid sample side of each strip at the fluid sample application site while simultaneously adding 15 µl of total bilirubin reagent (Sigma Catalog No. 550-4, reconstituted with sodium nitrite as directed by the manufacturer except a 20×concentrated reagent solution was used) to the diluent solution side of the strip at the diluent solution application site. In each case, the two liquids flowed towards each other and upon meeting formed a discrete interface. The reaction product, azobilirubin, developed at the product interface. FIG. 26 is a digital photograph of the 4.73 mg/dl. FIG. 26 shows product formation at 15 seconds and 275 seconds after sample application to the test strip. These digital images were recorded as described for Example 3. FIG. 26 shows that the assay performed in accordance with the subject invention produces a substantial color intensity within 15 seconds from application of the sample to the test strip of the present invention.

EXAMPLE 8

This example illustrates how the present invention was applied to detect and quantify uric acid in fetal calf serum. In this example, samples ranging between 0.15 mg/dl and 15.5 mg/dl samples were used.

Figure 27:
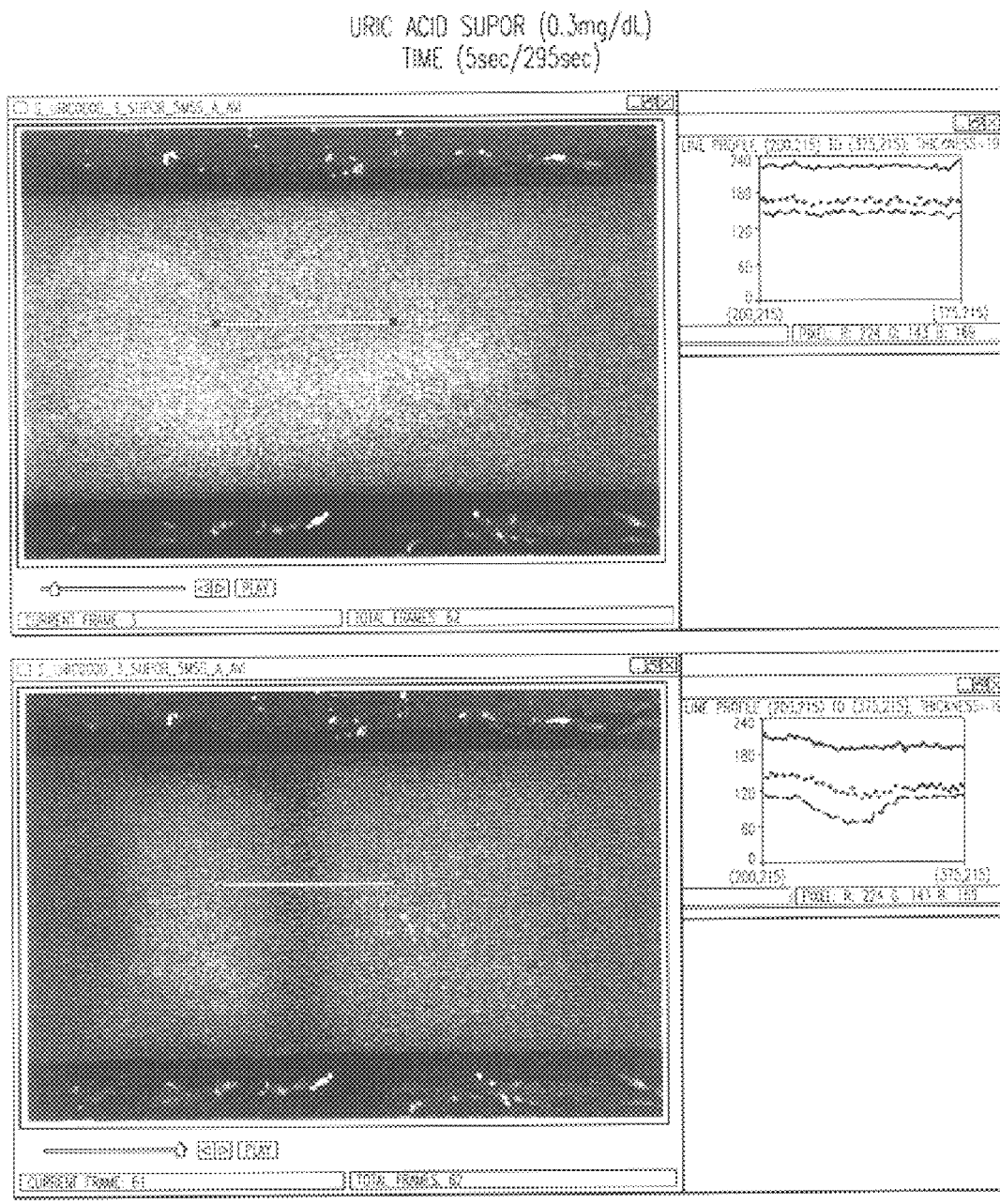
FIG. 27 is a digital color image of an assay for uric acid run in accordance with the method of the present invention at a concentration of 0.3 mg/dl uric acid, and measured at 5 seconds and 295 seconds after sample application, as well as the associated color absorption graph for a selected portion of the digital color image at each time point.

Polyethersulfone membranes were prepared as described in Example 1 and washed with water at pH 7.0. Fifteen microliters of fetal calf serum containing 0.15 mg/dl, 0.3 mg/dl, 0.6 mg/dl, 1.0 mg/dl, 3.7 mg/dl, 7.3 mg/dl, and 15.5 mg/dl of uric acid was added to the fluid sample side of each strip at the fluid sample application site while simultaneously adding 15 µl of uric acid reagent (Sigma Catalog No. 685 except a 3.3×concentrated reagent solution was used) to the diluent solution side of the strip at the diluent solution application site. In each case, the two liquids flowed towards each other and upon meeting formed a discrete interface. The reaction product, a quinoneimine dye having an maximal absorption at 520 nm, developed at the product interface. FIG. 27 is a digital photograph of the 0.3 mg/dl test strip showing product formation within 5 seconds and 295 seconds after sample application to the test strip. These digital images were recorded as described for Example 3, and show a substantial product intensity developed after 295 seconds.

EXAMPLE 9

This example illustrates how the present invention was applied to detect and quantify γ-glutamyl transferase in fetal calf serum. In this example, samples ranging between 8 Units/liter (U/L) and 725 U/L samples were used.

Figure 28:
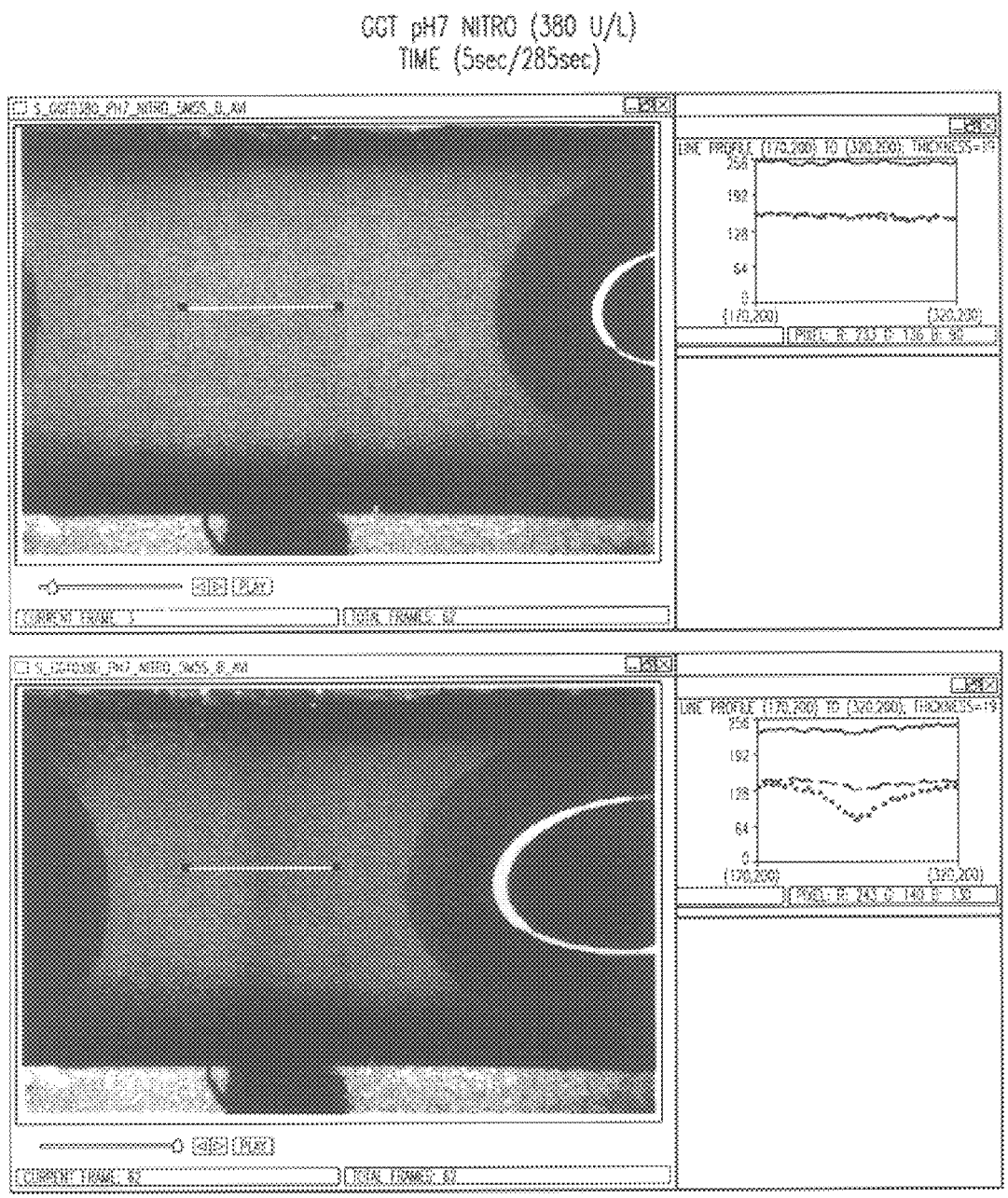
FIG. 28 is a digital color image of an assay for γ-glutamyl transferase activity run in accordance with the method of the present invention at a concentration of 380 U/l of γ-glutamyl transferase activity, and measured at 15 seconds and 285 seconds after sample application, as well as the associated color absorption graph for a selected portion of the digital color image at each time point.

Nitrocellulose membranes were washed with water at pH 7.0. Fifteen microliters of fetal calf serum containing 8, 37, 107, 380, and 725 U/L of γ-glutamyl transferase was added to the fluid sample application site while simultaneously adding 15 µl of γ-glutamyl transferase reagent (Sigma Catalog No. 419, prepared according to the manufacturer's instructions except a 2×concentrated reagent solution was used) to the diluent solution side of the strip at the diluent solution application site. In each case, the two liquids flowed towards each other and upon meeting formed a discrete interface. The reaction product, 5-amino-2-nitrobenzoate, having an maximal absorption at 405 nm, developed at the product interface. FIG. 28 is a digital photograph of the 380 U/L test strip showing product formation 5 seconds and 285 seconds after sample application to the test strip. These digital images were recorded as described for Example 3, and show that a substantial product development occurred after 285 seconds.

EXAMPLE 10

This example illustrates how the present invention was applied to detect and quantify amylase in fetal calf serum. In this example, samples ranging between 88 Units/liter (U/L) and 16,800 U/L samples were used.

Figure 29:
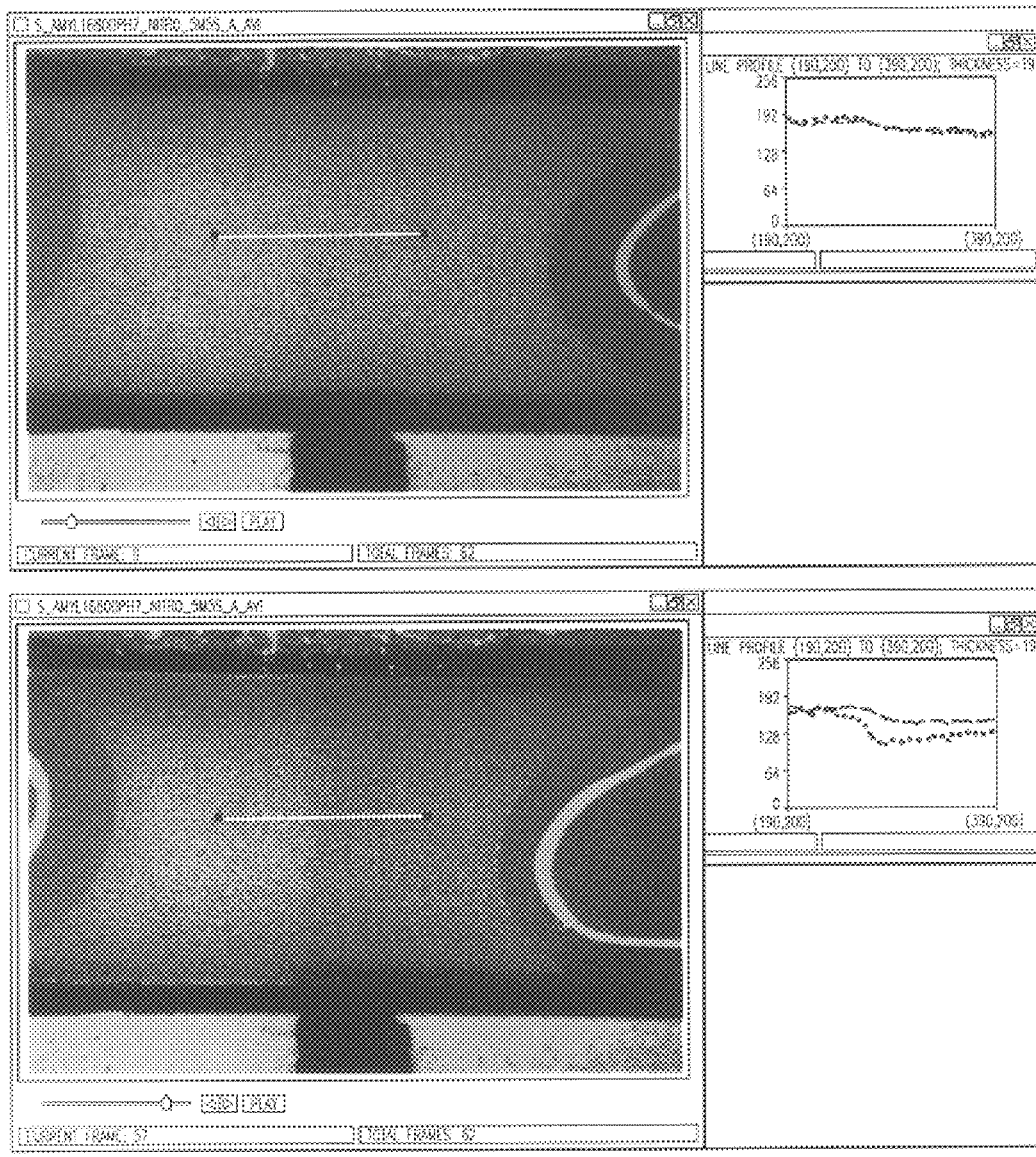
FIG. 29 is a digital color image of an assay for amylase run in accordance with the method of the present invention at a concentration of 16,800 U/l amylase, and measured at 35 seconds and 275 seconds after sample application, as well as the associated color absorption graph for a selected portion of the digital color image at each time point.

Nitrocellulose membranes were washed with water at pH 7.0. Fifteen microliters of fetal calf serum containing 88, 362, 1,680, and 16,800 U/L of amylase was added to the fluid sample application site, while simultaneously adding 15 µl of amylase reagent (Sigma Catalog No. 419, prepared according to the manufacturer's instructions except a 2×concentrated reagent solution was used) to the diluent solution side of the strip at the diluent solution application site. In each case, the two liquids flowed towards each other and upon meeting formed a discrete interface. The reaction product, p-nitrophenol, having an maximal absorption at 405 nm, developed at the product interface. FIG. 29 is a digital photograph of the 16,800 U/L test strip showing product formation 35 seconds and 275 seconds after sample application to the test strip. These digital images were recorded as described for Example 3. A significant level of product development occurred after 275 seconds.

EXAMPLE 11

This example illustrates how the present invention was applied to detect and quantify creatinine in fetal calf serum. In this example, samples ranging between 75 mg/dl and 300 mg/dl were used.

Figure 30:
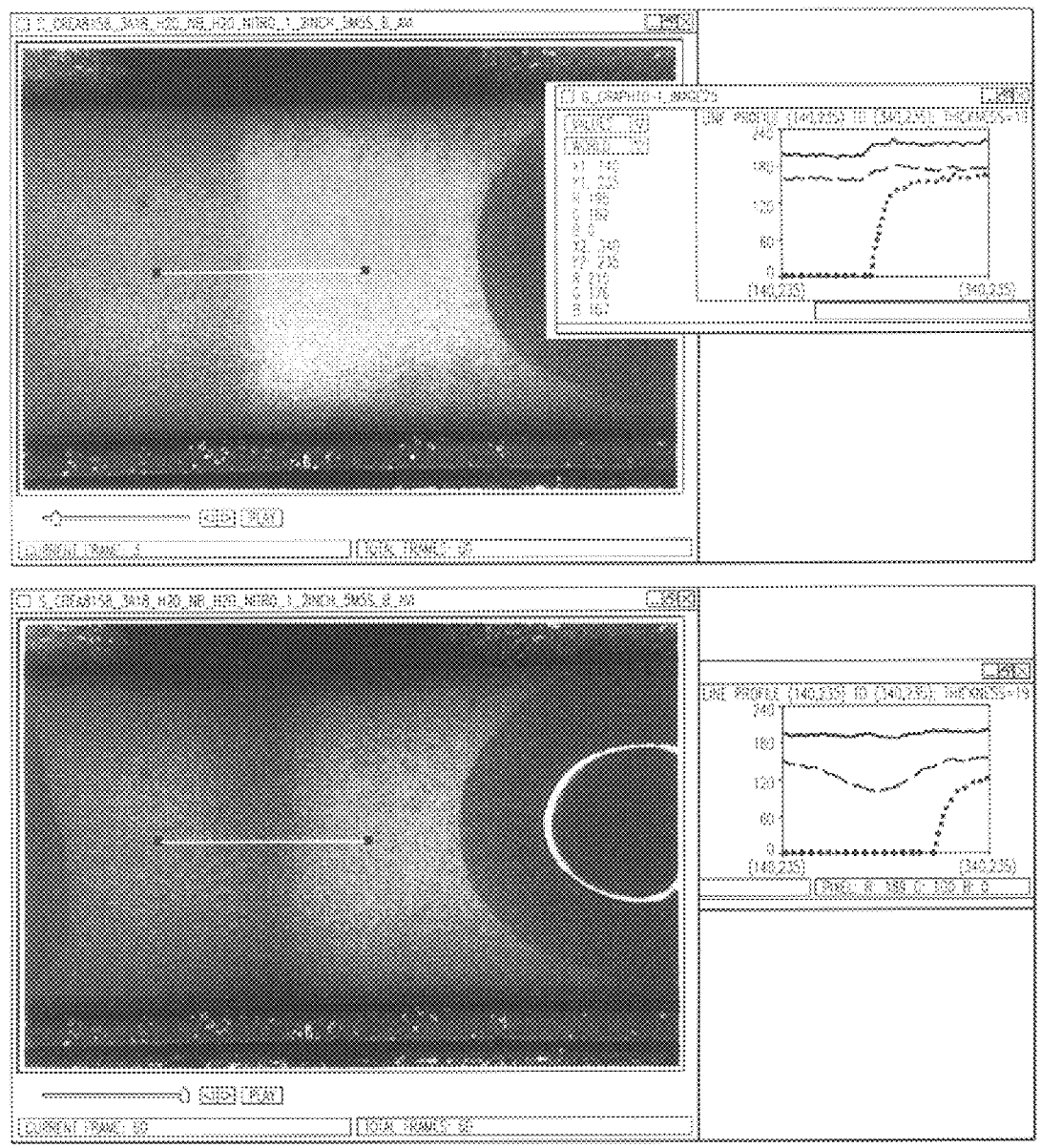
FIG. 30 is a digital color image of an assay for creatinine run in accordance with the method of the present invention at a concentration of 150mg/dl creatinine, and measured at 5 seconds and 295 seconds after sample application, as well as the associated color absorption graph for a selected portion of the digital color image at each time point.

Nitrocellulose membranes were washed with water at pH 7.0. Fifteen microliters of fetal calf serum containing 75 mg/dl, 150 mg/dl, and 300 mg/dl of creatinine was added to the fluid sample application site, while simultaneously adding 15 µl of creatinine reagent (Sigma Catalog No. 557-A and 557-B, prepared as instructed by the manufacturer except a 2×concentrated reagent solution was used) to the diluent solution side of the strip at the diluent solution application site. In each case, the two liquids flowed towards each other and upon meeting formed a discrete interface. The reaction product, a Janovski complex, having an maximal absorption between 480 and 520 nm, developed at the interface. FIG. 30 is a digital photograph of the 150 mg/dl test strip showing product formation 5 seconds and 295 seconds after sample application to the test strip. These digital images were recorded as described for Example 3, and show a significant level of the product formed after 295 seconds.

EXAMPLE 12

This example illustrates how the present invention was applied to detect and quantify cholesterol. In this example, samples ranging between 61 mg/dl and 183 mg/dl were used.

Figure 31:
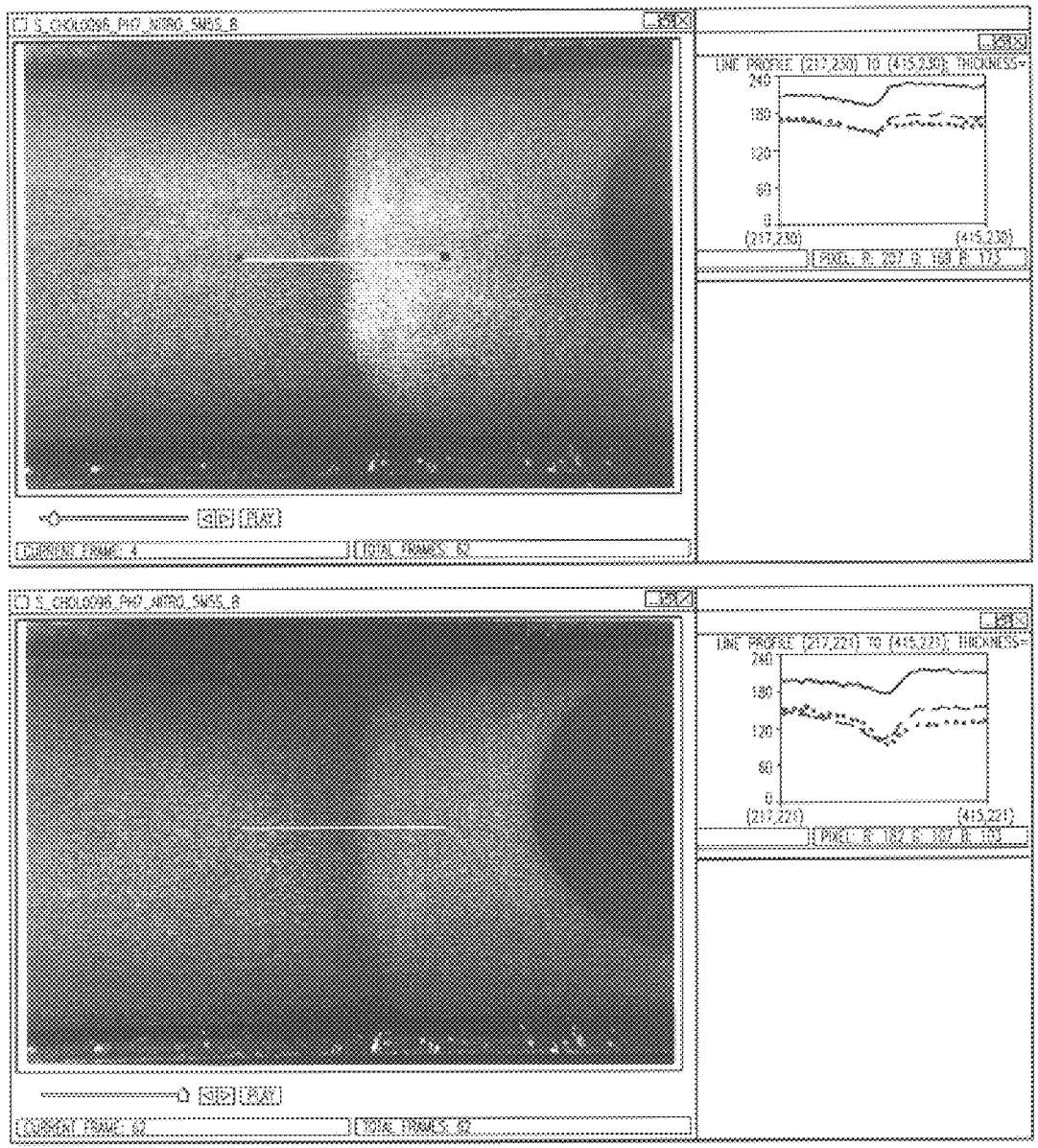
FIG. 31 is a digital color image of an assay for cholesterol run in accordance with the method of the present invention at a concentration of 96 mg/dl cholesterol, and measured at 10 seconds and 300 seconds after sample application, as well as the associated color absorption graph for a selected portion of the digital color image at each time point.

Nitrocellulose membranes were washed with water at pH 7.0. Fifteen microliters of a commercial cholesterol standard solution containing 61 mg/dl, 96 mg/dl, 160 mg/dl, or 183 mg/dl of cholesterol was added to the fluid sample application site, while simultaneously adding 15 μl of cholesterol reagent (Sigma Catalog No. 352) to the diluent solution side of the strip at the diluent solution application site. In each case, the two liquids flowed towards each other and upon meeting formed a discrete interface. The reaction product, a quinoneimine dye having an maximal absorption at 500 nm, developed at the product interface. FIG. 31 is a digital photograph of the 96 mg/dl test strip showing product formation 10 seconds and 300 seconds after sample application to the test strip. These digital images were recorded as described for Example 3. A detectable level of product was formed within 10 seconds after sample application to the test strip, and had increased substantially after 300 seconds.

EXAMPLE 13

This example shows how the present invention was applied to detect and quantify total protein. In this example, samples ranging between 2.1 g/dl and 8.2 g/dl were used.

Figure 32:
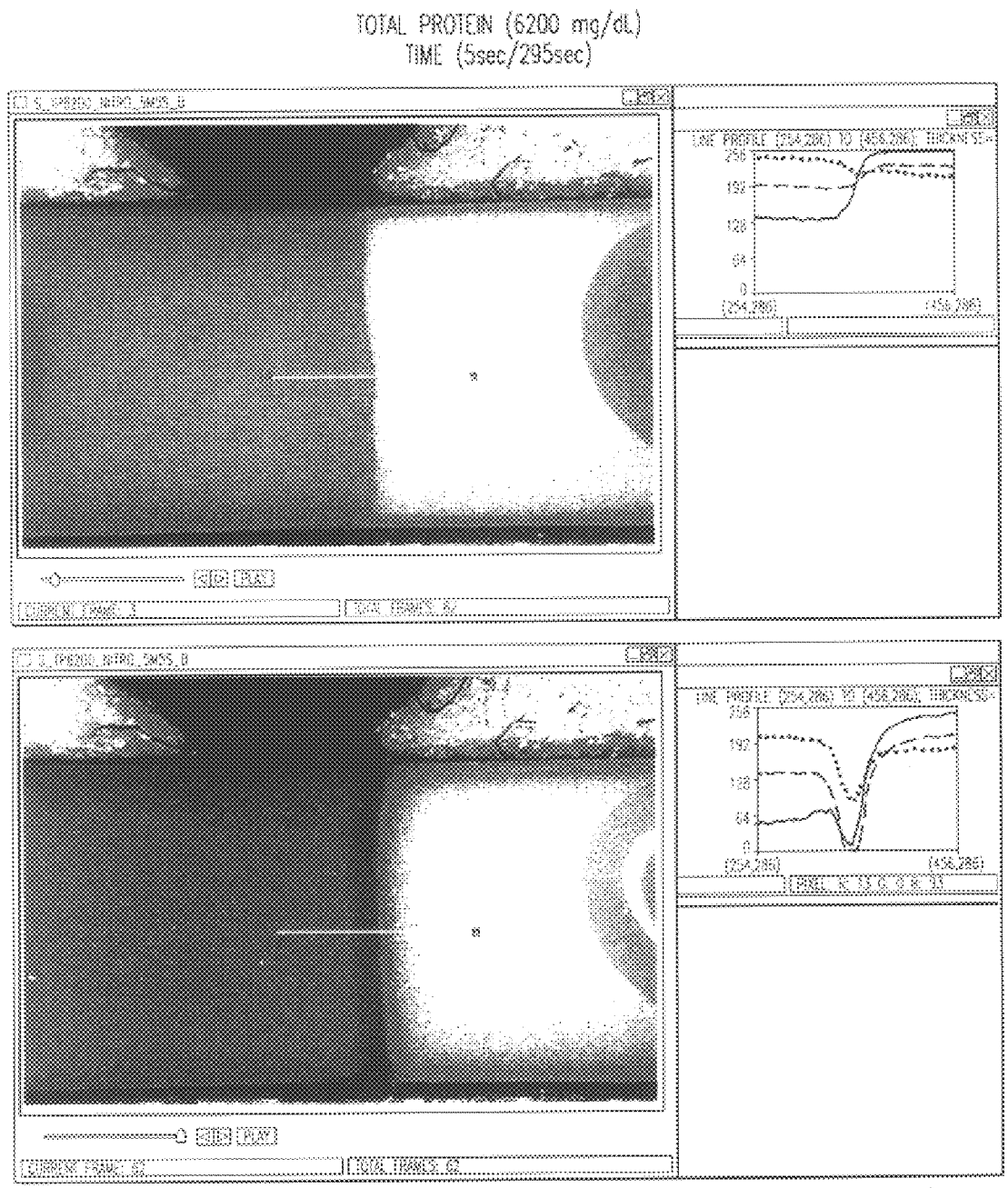
FIG. 32 is a digital color image of an assay for total protein run in accordance with the method of the present invention at a concentration of 6,200 mg/dl total protein, and measured at 5 seconds and 295 seconds after sample application, as well as the associated color absorption graph for a selected portion of the digital color image at each time point.

Nitrocellulose membranes were washed with water at pH 7.0. Fifteen microliters of fetal calf or dog serum containing 2.1 g/dl, 4.1 g/dl, 6.2 g/dl and 8.2 g/dl total protein was added to the fluid sample application site, while simultaneously adding 15 μl of alkaline biuret reagent (Sigma Catalog No. 541, prepared according to the manufacturer's instructions except a 15×concentrated reagent solution was used) to the diluent solution side of the strip at the diluent solution application site. In each case, the two liquids flowed towards each other and upon meeting formed a discrete interface. The reaction product, a purple copper-protein complex having an maximal absorption at 540 nm, developed at the product interface. FIG. 32 is a digital photograph of the 6.2 g/dl test strip showing product formation 5 seconds and 295 seconds after sample application to the test strip. These digital images were recorded as described for Example 3. A significant level of product was detectable after 5 seconds, and a substantial amount of product was formed after 295 seconds.

EXAMPLE 14

This example illustrating how the present invention was applied to detect and quantify magnesium in fetal calf serum. In this example, a sample containing 4.7 mg/dl magnesium was used.

Figure 33:
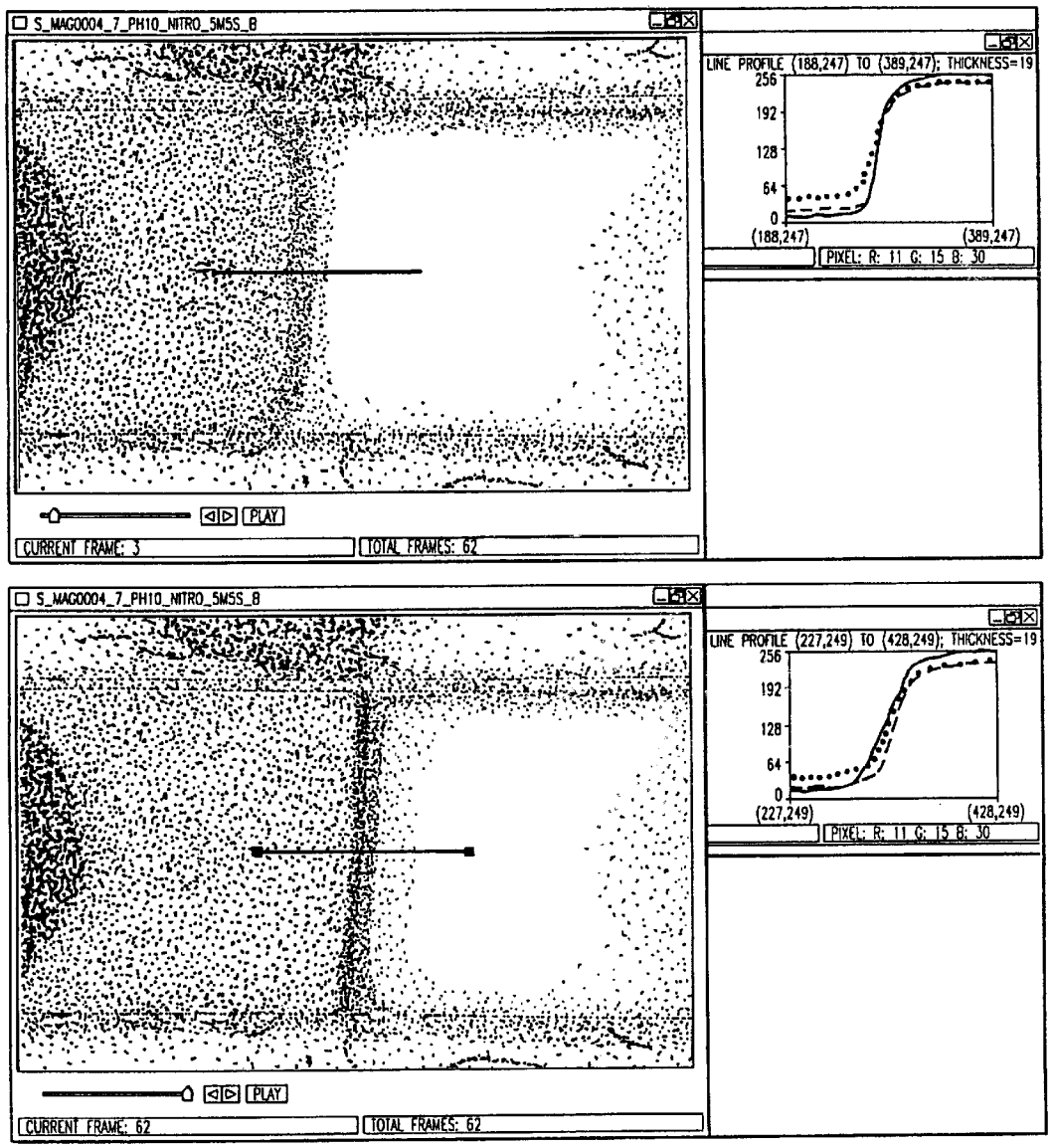
FIG. 33 is a digital color absorption image of an assay for magnesium run in accordance with the method of the present invention at a concentration of 4.7 mg/dl magnesium, and measured at 5 seconds and 295 seconds after sample application, as well as the associated UV absorption graph for a selected portion of the digital UV absorption image at each time point.

Nitrocellulose membranes were washed with dilute NaOH at pH 10.0. Fifteen microliters of fetal calf serum containing 4.7 mg/dl of magnesium was added to the fluid sample application site, while simultaneously adding 15 μl of magnesium reagent (Sigma Catalog No. 595, prepared as described by the manufacturer except a large excess of magnesium reagent (≈100×) was used) to the diluent solution side of the strip at the diluent solution application site. In each case, the two liquids flowed towards each other and upon meeting formed a discrete interface. The reaction product, a calmagite-magnesium complex having an maximal absorption at 520 nm, developed at the product interface. FIG. 33 is a digital photograph of the 4.7 mg/dl test strip showing product formation 5 seconds and 295 seconds after sample application to the test strip. These digital images were recorded as described for Example 3. The product was detectable after 5 seconds, and was substantial after 295 seconds.

EXAMPLE 15

This example illustrating how the present invention was applied to detect and quantify lactate dehydrogenase in fetal calf serum. In this example, samples ranging between 453 Units/liter (U/L) and 9,000 U/L samples were used.

Nitrocellulose membranes were washed with water at pH 7.0. Fifteen microliters of fetal calf serum containing 453, 905, 4,000 and 9,470 U/L of amylase was added to the fluid sample application site, while simultaneously adding 15 μl of lactate dehydrogenase reagent (Sigma Catalog No. 228, prepared according to the manufacturer's instructions except a 2×concentrated reagent solution was used) to the diluent solution side of the strip at the diluent solution application site. In each case, the two liquids flowed towards each other and upon meeting formed a discrete interface. The reaction product, reduced nicotinamide adenine dinucleotide (NADH), having a maximal absorption at 340 nm, developed at the product interface. FIG. 34 is a digital photograph of the 4.7 mg/dl test strip showing product formation 5 seconds and 295 seconds after sample application to the test strip. These digital images were recorded as described for Example 3. The product was detectable after 65 seconds, and a significant amount of product formed after 295 seconds.

What is claimed is:

1. A method for detecting and quantifying at least one analyte in a fluid sample suspected of containing the analyte by employing a liquid reactant that reacts with the analyte to form a detectable reaction product, by relating the analyte to the detectable reaction product of analyte and liquid reactant comprising:

providing a fluid transport material that absorbs a liquid and supports capillary flow of the liquid, the fluid transport material having a first zone for the application of the fluid sample suspected of containing the analyte, and a second zone for the application of the liquid reactant;

adding the fluid sample to the first zone, and the liquid reactant to the second zone, wherein the fluid sample thereafter flows in a first direction from a fluid sample edge toward the second zone, and the liquid reactant flows in a second direction opposite to that of the first direction and toward the first zone from a liquid reactant edge;

whereby when the flowing fluid sample and the flowing liquid reactant meet, flow stops and the detectable reaction product is formed by a reaction between the liquid reactant and the analyte, and a stable reaction interface is formed at a juncture between and visually distinct from the fluid sample and the liquid reactant; and detecting the detectable reaction product.

2. The method of claim 1, wherein the fluid transport material separates red blood cells from whole blood.

3. The method of claim 2, wherein the fluid transport material is comprised of a material selected from the group consisting of: nitrocellulose, cellulose, polyethylene, polystyrene, polypropylene, and polyethersulfone.

4. The method of claim 1, wherein at least one of the first zone and the second zone contains a reagent.

5. The method of claim 1, wherein the fluid transport material is a nitrocellulose material cast on a backing material.

6. The method of claim 5, wherein the backing material is comprised of polyvinylchloride or polyester.

7. The method of claim 1, further comprising providing a pad located on the first zone.

8. The method of claim 7, wherein the pad is effective to remove red blood cells from the fluid sample.

9. The method of claim 7, wherein the pad is made of glass fiber or polyester.

10. The method of claim 1, further comprising measuring an amount of the detectable reaction product.

11. The method of claim 10, wherein the step of measuring an amount of the detectable reaction product includes measuring a member selected from the group consisting of absorbance, reflectance, transmission, fluorescence, luminescence, and conductance.

12. The method of claim 10, wherein the detectable reaction product is measured by absorbance or reflectance.

13. The method of claim 12, wherein the absorbance or reflectance is measured at one or more wavelengths of $\geq 250$ nanometers.

14. The method of claim 1, wherein an amount of the detectable reaction product is proportional to a concentration of the analyte based on a peak intensity of reflectance or absorption of the detectable reaction product.

15. The method of claim 1, wherein the detectable reaction product is formed at a rate that is proportional to the concentration of the analyte.

16. The method of claim 15, wherein the rate is calculated as a change over time of a peak intensity of reflectance or absorption of the detectable reaction product.

17. The method of claim 16, wherein the peak intensity of reflectance or absorption is measured across a line substantially perpendicular to the reaction interface.

18. The method of claim 16, wherein the peak intensity of reflectance or absorption is measured within a polygonal region encompassing all or a portion of the reaction interface.

19. The method of claim 1, wherein the detectable reaction product is formed in an amount greater than or equal to a predetermined threshold intensity of reflectance or absorption indicative of the presence of the analyte.

20. The method of claim 1, further comprising measuring a member selected from the group consisting of: a distance between the fluid sample edge and a midpoint of the stable reaction interface, a distance between the liquid reactant edge and a midpoint of the stable reaction interface, a distance between the fluid sample edge and a midpoint of a stable liquid interface, a distance between the liquid reactant edge and a midpoint of a stable liquid interface, a distance between the midpoint of the stable reaction interface and the midpoint of a stable liquid interface, a reflectance or absorption of the detectable reaction product at a plurality of fixed time points, a reflectance or absorption of the stable liquid interface at a plurality of fixed time points, a rate of change of the reflectance or absorption of the detectable reaction product, an area of the stable reaction interface, an area of the stable liquid interface, a background level of the fluid sample, and a background level of the liquid reactant.

21. The method of claim 1, wherein the at least one analyte includes a member selected from the group consisting of glucose, calcium, albumin, alkaline phosphatase, ammonia, bilirubin, uric acid, γ-glutamyl transferase, amylase, creatine kinase, creatinine, cholesterol, total protein, magnesium, lactate dehydrogenase, lipase, phosphorus, triglyceride, alanine aminotransferase, asparatate aminotransferase, and blood urea nitrogen.

22. The method of claim 1, further comprising calibrating a concentration of the liquid reagent by applying an amount of the analyte to a calibration zone, the calibration zone being located between the first zone and the reaction interface, whereby when the amount of the analyte is added to the calibration zone, the analyte in the amount of analyte flows in a first direction toward the second zone, and the liquid reactant flows in a second direction opposite to that of the first direction and toward the first zone from a liquid reactant edge;

whereby the flowing analyte in the amount of the analyte and the flowing liquid reactant meet, flow stops and a detectable calibration product is formed by a reaction between the analyte in the amount of the analyte and the liquid reactant, and a stable calibration reaction interface is formed at a juncture between and visually distinct from the analyte in the amount of the analyte and the liquid reactant; and detecting the detectable reaction product.

23. The method of claim 22, wherein the amount of the analyte added to the calibration zone is in excess of the amount of the analyte in the fluid sample, such that the amount of the analyte added to the calibration zone is sufficient to form an amount of the calibration product that enables determination of an amount of the liquid reactant.

24. The method of claim 22, wherein the detectable calibration product is formed at a rate that is proportional to a concentration of the analyte.

25. The method of claim 24, wherein the rate is calculated as a change over time of a peak intensity of reflectance or absorption of the detectable calibration product.

26. The method of claim 25, wherein the peak intensity of reflectance or absorption is measured across a line substantially perpendicular to the calibration interface.

27. The method of claim 25, wherein the peak intensity of reflectance or absorption is measured within a polygonal region encompassing all or a portion of the calibration interface.

28. The method of claim 22, wherein the detectable reaction product is formed in an amount greater than or equal to a predetermined threshold intensity of reflectance or absorption indicative of the presence of the analyte.

29. A method for detecting and quantifying at least one analyte in a fluid sample suspected of containing the analyte by employing a liquid reactant that reacts with the analyte to form a detectable reaction product, by relating the analyte to the detectable reaction product of analyte and liquid reactant comprising:

providing a fluid transport material that absorbs a liquid and supports capillary flow of the liquid, the fluid transport material having a first zone for the application of the fluid sample suspected of containing the analyte, and a second zone for the application of a liquid to a pad containing a reconstitutable reagent, wherein when the fluid sample is added to the first zone, and the liquid is added to the second zone, the fluid sample flows in a first direction from a fluid sample edge toward the second zone, the reagent is reconstituted and the reagent and the liquid form a liquid reagent containing a liquid reactant that reacts with the analyte to form a detectable reaction product, and the liquid reactant flows in a second direction opposite to that of the first direction and toward the first zone from a liquid reactant edge;

whereby when the flowing fluid sample and the flowing liquid reactant meet, flow stops and the detectable reaction product is formed by a reaction between the liquid reactant and the analyte, and a stable reaction interface is formed at a juncture between and visually distinct from the fluid sample and the liquid reactant; and detecting the detectable reaction product.

30. The method of claim 29, wherein the fluid transport material separates red blood cells from whole blood.

31. The method of claim 30, wherein the fluid transport material is comprised of a material selected from the group consisting of: nitrocellulose, cellulose, polyethylene, polystyrene, polypropylene, and polyethersulfone.

32. The method of claim 29, wherein at least one of the first zone and the second zone contains a reagent.

33. The method of claim 29, wherein the fluid transport material is a nitrocellulose material cast on a backing material.

34. The method of claim 33, wherein the backing material is comprised of polyvinylchloride or polyester.

35. The method of claim 29, further comprising providing a pad located on the first zone.

36. The method of claim 35, wherein the pad is effective to remove red blood cells from the fluid sample.

37. The method of claim 35, wherein the pad is comprised of glass fiber or polyester.

38. The method of claim 29, further comprising measuring an amount of the detectable reaction product.

39. The method of claim 38, wherein the step of measuring an amount of the detectable reaction product includes measuring a member selected from the group consisting of absorbance, reflectance, transmission, fluorescence, luminescence, and conductance.

40. The method of claim 38, wherein the detectable reaction product is measured by absorbance or reflectance.

41. The method of claim 40, wherein the absorbance or reflectance is measured at one or more wavelengths of $\geq 250$ nanometers.

42. The method of claim 29, wherein an amount of the detectable reaction product is proportional to a concentration of the analyte based on a peak intensity of reflectance or absorption of the detectable reaction product.

43. The method of claim 29, wherein the detectable reaction product is formed at a rate that is proportional to the concentration of the analyte.

44. The method of claim 43, wherein the rate is calculated as a change over time of a peak intensity of reflectance or absorption of the detectable reaction product.

45. The method of claim 44, wherein the peak intensity of reflectance or absorption is measured across a line substantially perpendicular to the reaction interface.

46. The method of claim 44, wherein the peak intensity of reflectance or absorption is measured within a polygonal region encompassing all or a portion of the reaction interface.

47. The method of claim 29, wherein the detectable reaction product is formed in an amount greater than or equal to a predetermined threshold intensity of reflectance or absorption indicative of the presence of the analyte.

48. The method of claim 29, wherein the detectable reaction product is formed at a rate sufficient for it to be detected within about fifteen seconds after application of the fluid sample to the fluid sample zone.

49. The method of claim 29, further comprising measuring a member selected from the group consisting of: a distance between the fluid sample edge and a midpoint of the stable reaction interface, a distance between the liquid reactant edge and a midpoint of the stable reaction interface, a distance between the fluid sample edge and a midpoint of a stable liquid interface, a distance between the liquid reactant edge and a midpoint of a stable liquid interface, a distance between the midpoint of the stable reaction interface and the midpoint of a stable liquid interface, a reflectance or absorption of the detectable reaction product at a plurality of fixed time points, a reflectance or absorption of the stable liquid interface at a plurality of fixed time points, a rate of change of the reflectance or absorption of the detectable reaction product, an area of the stable reaction interface, an area of the stable liquid interface, a background level of the fluid sample, and a background level of the liquid reactant.

50. The method of claim 29, wherein the at least one analyte includes a member selected from the group consisting of: glucose, calcium, albumin, alkaline phosphatase, ammonia, bilirubin, uric acid, γ-glutamyl transferase, amylase, creatine kinase, creatinine, cholesterol, total protein, magnesium, lactate dehydrogenase, lipase, phosphorus, triglyceride, alanine aminotransferase, asparatate aminotransferase, and blood urea nitrogen.

51. The method of claim 29, further comprising calibrating a concentration of the liquid reagent by applying an amount of the analyte to a calibration zone, the calibration zone being located between the first zone and the reaction interface, whereby when the amount of the analyte is added to the calibration zone, the analyte in the amount of the analyte flows in a first direction toward the second zone, and the liquid reactant flows in a second direction opposite to that of the first direction and toward the first zone from a liquid reactant edge;

whereby the flowing analyte in the amount of the analyte and the flowing liquid reactant meet, flow stops and a detectable calibration product is formed by a reaction between the analyte in the amount of the analyte and the liquid reactant, and a stable calibration reaction interface is formed at a juncture between and visually distinct from the analyte in the amount of the analyte and the liquid reactant, the calibration interface further being adjacent to the reaction interface; and measuring the calibration product at the same at least one desired wavelength of reflectance or absorbance as the reaction product.

52. The method of claim 51, wherein the amount of the analyte added to the calibration zone is in excess of the amount of the analyte in the fluid sample, such that the amount of the analyte added to the calibration zone is sufficient to form an amount of the calibration product that enables determination of an amount of the liquid reactant.

53. The method of claim 51, wherein the detectable calibration product is formed at a rate that is proportional to the concentration of the analyte.

54. The method of claim 53, wherein the rate is calculated as a change over time of a peak intensity of reflectance or absorption of the detectable calibration product.

55. The method of claim 54, wherein the peak intensity of reflectance or absorption is measured across a line substantially perpendicular to the reaction interface.

56. The method of claim 54, wherein the peak intensity of reflectance or absorption is measured within a polygonal region encompassing all or a portion of the reaction interface.

57. The method of claim 51, wherein the detectable reaction product is formed in an amount greater than or equal to a predetermined threshold intensity of reflectance or absorption indicative of the presence of the analyte.

* * * * *